US008124589B2

(12) United States Patent
Henderson

(10) Patent No.: US 8,124,589 B2
(45) Date of Patent: Feb. 28, 2012

(54) USE OF KETOGENIC COMPOUNDS FOR TREATMENT OF AGE-ASSOCIATED MEMORY IMPAIRMENT

(75) Inventor: Samuel T. Henderson, Broomfield, CO (US)

(73) Assignee: Accera, Inc., Broomfield, CO (US)

( * ) Notice: Subject to any disclaimer, the term of this patent is extended or adjusted under 35 U.S.C. 154(b) by 74 days.

(21) Appl. No.: 12/064,850

(22) PCT Filed: Apr. 3, 2007

(86) PCT No.: PCT/US2007/065873
§ 371 (c)(1),
(2), (4) Date: Apr. 24, 2008

(87) PCT Pub. No.: WO2007/115282
PCT Pub. Date: Oct. 11, 2007

(65) Prior Publication Data
US 2008/0287372 A1 Nov. 20, 2008

Related U.S. Application Data

(63) Continuation-in-part of application No. 11/021,920, filed on Dec. 22, 2004, which is a continuation of application No. 10/152,147, filed on May 20, 2002, now Pat. No. 6,835,750, which is a continuation-in-part of application No. 09/845,741, filed on May 1, 2001.

(60) Provisional application No. 60/744,140, filed on Apr. 3, 2006, provisional application No. 60/200,980, filed on May 1, 2000.

(51) Int. Cl.
*A61K 31/225* (2006.01)
*A61K 31/23* (2006.01)
*A61K 31/7004* (2006.01)
*A61P 3/00* (2006.01)

(52) U.S. Cl. .......................................... 514/23; 514/547

(58) Field of Classification Search .................. None
See application file for complete search history.

(56) References Cited

U.S. PATENT DOCUMENTS

| 2,766,145 A | 10/1956 | O'Brien |
| 2,766,146 A | 10/1956 | Gilbert |
| 3,053,677 A | 9/1962 | Touey |
| 4,346,107 A | 8/1982 | Cavazza et al. |
| 4,407,821 A | 10/1983 | Mendy |
| 4,528,197 A | 7/1985 | Blackburn |
| 4,551,523 A | 11/1985 | Elam |
| 4,847,296 A | 7/1989 | Babayan et al. |
| 5,093,044 A | 3/1992 | Wretlind |
| 5,276,059 A | 1/1994 | Caughey et al. |
| 5,308,832 A | 5/1994 | Garleb et al. |
| 5,385,915 A | 1/1995 | Buxbaum et al. |
| 5,391,375 A | 2/1995 | Hille et al. |
| 5,504,072 A | 4/1996 | Schmidt et al. |
| 5,508,167 A | 4/1996 | Rose's et al. |
| 5,538,983 A | 7/1996 | Buxbaum et al. |
| 5,614,560 A | 3/1997 | Lipton |
| 5,650,148 A | 7/1997 | Gage et al. |
| 5,691,325 A * | 11/1997 | Sandyk .................... 514/159 |
| 5,716,828 A | 2/1998 | Rose's et al. |
| 5,817,626 A | 10/1998 | Findeis et al. |
| 5,854,204 A | 12/1998 | Findeis et al. |
| 5,854,215 A | 12/1998 | Findeis et al. |
| 5,925,684 A | 7/1999 | Schweikert et al. |
| 5,935,781 A | 8/1999 | Poirier |
| 5,936,078 A | 8/1999 | Kuga et al. |
| 5,980,939 A | 11/1999 | Kim et al. |
| 6,027,896 A | 2/2000 | Rose's et al. |
| 6,136,862 A | 10/2000 | Hiraide et al. |
| 6,207,856 B1 | 3/2001 | Veech |
| 6,232,345 B1 | 5/2001 | Hiraide et al. |
| 6,316,038 B1 | 11/2001 | Veech |
| 6,323,237 B1 | 11/2001 | Veech |
| 6,380,244 B2 | 4/2002 | Martin |
| 6,395,306 B1 | 5/2002 | Cui et al. |
| 6,835,750 B1 * | 12/2004 | Henderson .................... 514/557 |
| 6,884,454 B2 | 4/2005 | Pimentel |
| 7,001,736 B1 | 2/2006 | Poirier |
| 7,049,078 B2 | 5/2006 | Poirier |

(Continued)

FOREIGN PATENT DOCUMENTS

EP      0519727      12/1992

(Continued)

OTHER PUBLICATIONS

Van Dongen et al., J Am Geriatr Soc, "The efficacy of ginkgo for elderly people with dementia and age-associated memory impairment: new results of a randomized clinical trial", vol. 48, issue 10, pp. 1183-1194 (2000).*
Article World "human weight"; also available at http://www.articleworld.org/index.php?title=Human_weight&printable=yes; last viewed Apr. 6, 2010.*
Small et al., Proc. Natl. Acad. Sci. "Cerebral metabolic and cognitive decline in persons at genetic risk for Alzheimer's disease", vol. 97, issue 11, pp. 6037-6042 (2000).*

(Continued)

*Primary Examiner* — Shaojia Anna Jiang
*Assistant Examiner* — Bahar Schmidtmann
(74) *Attorney, Agent, or Firm* — Swanson & Bratschun, L.L.C.

(57) ABSTRACT

This invention relates to the field of therapeutic agents for the treatment of Age-Associated Memory Impairment (AAMI). In particular, the present invention utilizes compositions comprising at least one compound capable of elevating ketone body concentrations in a mammal (e.g., ketogenic compounds), administered in an amount effective for treatment or prevention of loss of cognitive function caused by reduced neuronal metabolism in AAMI. In one embodiment, the composition includes medium chain triglycerides (MCT). In another embodiment, the compositions are administered in the presence of carbohydrate. The present invention also relates to oral dosage forms, in particular, a nutritional drink comprising at least one compound capable of elevating ketone body concentrations in a mammal.

23 Claims, 2 Drawing Sheets

U.S. PATENT DOCUMENTS

| | | | |
|---|---|---|---|
| 7,087,649 | B2 | 8/2006 | Barth et al. |
| 2001/0041736 | A1 | 11/2001 | Veech |
| 2002/0006959 | A1* | 1/2002 | Henderson ................ 514/552 |
| 2002/0103139 | A1 | 8/2002 | Weisspapir et al. |
| 2003/0059824 | A1 | 3/2003 | Henderson |
| 2004/0052926 | A1 | 3/2004 | Apfelbaum |
| 2004/0058873 | A1 | 3/2004 | Esmond et al. |
| 2004/0060077 | A1 | 3/2004 | Esmond |
| 2005/0013884 | A1 | 1/2005 | Rennels |
| 2005/0031651 | A1 | 2/2005 | Gervais |
| 2005/0043242 | A1 | 2/2005 | Esmond |
| 2006/0122270 | A1 | 6/2006 | Henderson |
| 2006/0134240 | A1 | 6/2006 | Miljkovic |
| 2006/0280721 | A1 | 12/2006 | Veech et al. |
| 2008/0287372 | A1 | 11/2008 | Henderson |

FOREIGN PATENT DOCUMENTS

| | | |
|---|---|---|
| EP | 0676205 | 10/1995 |
| EP | 0808626 | 11/1997 |
| GB | 2368011 | 4/2002 |
| JP | 6-287138 | 6/1994 |
| JP | 06-287138 | * 10/1994 |
| JP | A-6287 138 | 10/1994 |
| JP | 3486778 | 1/2004 |
| WO | WO 91/15963 | 10/1991 |
| WO | WO 95/09146 | 4/1995 |
| WO | WO 96/14063 | 5/1996 |
| WO | WO 98/41200 | 9/1998 |
| WO | WO 98/41201 | 9/1998 |
| WO | WO 99/33853 | 7/1999 |
| WO | WO 99/51097 | 10/1999 |
| WO | WO 00/04895 | 2/2000 |
| WO | WO 00/15216 | 3/2000 |
| WO | WO 00/61079 | 10/2000 |
| WO | WO 01/82928 | 11/2001 |
| WO | WO 02/18400 | 3/2002 |
| WO | WO 02/053121 | 7/2002 |
| WO | WO 2004/077938 | 9/2004 |
| WO | WO 2004/108740 | 12/2004 |
| WO | WO2005/074970 | * 8/2005 |

OTHER PUBLICATIONS

Poirier et al., Proc. Natl. Acad. Sci. "Apolipoprotein E4 allele as a predictor of cholinergic deficits and treatment outcome in Alzheimer disease", vol. 92, issue 26, pp. 12260-12264 (1995).*
NutritionData "Seeds, sunflower seed kernels, toasted, without salt" (one ounce); also available at http://www.nutritiondata.com/facts/nut-and-seed-products/3079/2; last viewed Apr. 6, 2010.*
Wolff, Burgers Medicinal Chemistry and Drug Discovery Fifth Edition, vol. 1: Principles and Practice; pp. 975-977 (1995).*
Testa, Bernard, Biochemical Pharmacology "Prodrug research: futile or fertile?", vol. 68, pp. 2097-2106 (2004).*
Stella, Expert Opin. Ther. Patents "Prodrugs as therapeutics", vol. 14, issue 3, pp. 277-280 (2004).*
Ettmayer, Peter et al., Journal of Medicinal Chemistry "Lessons Learned from Marketed and Investigational Prodrugs", vol. 47, issue 10, pp. 2393-2404 (2004).*
Brosnan, J. T. and Brosnan, M. E., Journal of Nutrition "Branched-Chain Amino Acids: Metabolism, Physiological Function, and Application", vol. 136, issue 1, pp. 207S-211S (2006).*
DeCarli, Charles, Lancet Neurology, "Mild cognitive impairment: prevalance, prognosis, aetiology, and treatment", 2003, vol. 2, pp. 15-21.*
Reger et al. (2004) Neurobiology of Aging, 25:311-314, "Effects of β-hydroxybutyrate on cognition in memory-impaired adults".
Huttenlocher (1976) Pediatric Research, 10:536-540, "Ketonemia and Seizures: Metabolic and Anticonvulsant Effects of Two Ketogenic Diets in Childhood Epilepsy".
Pi-Sunyer et al. (Feb. 1969) Diabetes, 18(2):96-100, "Insulin and Ketone Responses to Ingestion of Medium and Long-chain Triglycerides in Man".
Notice of Opposition sent Dec. 28, 2009 by the European Patent Office for 01930965.7.
Babayan (1987) Lipids 22:417-20 "Medium Chain Triglycerides and Structured Lipids".

Bach et al. (1982) Amer. J. Clinic. Nutr. 36:950-962 "Medium-chain triglycerides: an update".
Bach (1996) J. Lipid Res. 37:708 "The usefulness of dietary medium-chain triglycerides in body weight control: fact or fancy?".
Beckman and Ames (1998) Physiol Rev. 78:547-81 "The Free Radical Theory of Aging Matures".
U.S. Appl. No. 11/021,920, filed Dec. 22, 2004, Henderson.
Beffert et al. (1998) Brain Research Reviews 27:119-142 "The neurobiology of apolipoproteins and their receptors in the CNS and Alzheimer's disease".
Blass et al. (1984) Neurochem Pathol 2:103-14 "Alzheimer's Disease: A Metabolic Systems Degeneration?".
Blass (2001) J. Neurosci Res. 66:851-6 "Brain Metabolism and Brain Disease: Is Metabolic Deficiency the Proximate Cause of Alzheimer Dementia?".
Blazquez et al. (1999) J. Neurochemistry 73:1674-1682 "The AMP-Activated Protein Kinase Is Involved in the Regulation of Ketone Body Production by Astrocytes".
Blazquez et al. (1999) J. Neurochemistry 72:1759-1768 "The Stimulation of Ketogenesis by Cannabinoids in Cultured Astrocytes Defines Carnitine Palitoyltransferase I as a New Ceramide-Activated Enzyme".
Blazquez et al. (1998) J. Neurochem. 71:1597-1606 "Role of carnitine palmitoyltransferase I in the control of ketogenesis in primary cultures of rat astrocytes".
Broer et al. (1997) J. Biol. Chem. 272:30096-102 "Comparison of Lactate Transport in Astroglial Cells and Monocarboxylate Transporter 1 (MCT 1) Expressing *Xenopus laevis* Oocytes".
Bruno et al. (1995) Alzheimer Disease and Associated Disorders (MEDLINE No. 96063810) Fall 9(3):128-31 "Acetyl-L-carnitine in Alzheimer disease: a short-term study on CSF neurotransmitters and neuropeptides".
Bullock (2002) Br J Psychiatry 180: 135-9 "New drugs for Alzheimer's disease and other dementias".
Corbo and Scacchi (1999) Ann Hum Genet 63:301-310 "Apolipoprotein E (APOE) allele distribution in the world. Is *APOE 4* a 'thrifty' allele?".
Cox et al. (1998) J. of Pediatrics 133(2):247-253 "Reversal of severe hypertrophic cardiomyopathy and excellent neuropsychologic outcome in very-long-chain acyl-coenzyme A dehydrogenase deficiency".
Craft et al. (1996) Neurobiology of Aging 17 (1):123-130 "Memory Improvement Following Induced Hyperinsulinemia in Alzheimer's Disease".
Cruz et al. (2001) J. Biol. Chem. 276:12162-12168 "Glucose and Insulin Stimulate Heparin-releasable Lipoprotein Lipase Activity in Mouse Islets and INS-1 Cells".
Davis et al. (1999) Nature 400:810 "Alois Alzheimer and the amyloid debate".
DeVries et al. (1997) Biochemistry 36:5285-5292 "Functional Characterization of Mitochondrial Carnitine Palmitoyltransferases I and II Expressed in the Yeast *Pichia pastoris*".
Dewachter et al. (2002) J Neurosci 22:3445-3453 "Neuronal deficiency of presenilin 1 inhibits amyloid plaque formation and corrects hippocampal long-term potentiation but not a cognitive defect of amyloid precursor protein [V717I] transgenic mice".
Dialog Results (Sep. 22, 2003) Agent for Prevention and/or therapeutics of Alzheimer's disease-contg. Triglyceride of 8-10 carbon fatty acids as active ingredient, Translation of Publication No. 06-287138.
Dias 1990 Metabolism 39:9:887 "Effects of Medium-Chain Triglyceride Feeding on Energy Balance in Adult Human".
Edmond (1992) Can J Physiol Pharmacol 70:S118-129 "Energy metabolism in developing brain cells".
Evans et al. (1989) JAMA 262 (18):2551-2556 "Prevalence of Alzheimer's Disease in a Community Population of Older Persons".
Finch et al. (1997) Experimental Neurology 143:82-102 "Aging, Metabolism, and Alzheimer Disease: Review and Hypotheses".
Frolich et al. (1998) J Neural Transm 105:423-438 "Brain insulin and insulin receptors in aging and sporadic Alzheimer's disease".
Gelman et al. (1999) Cell Mol Life Sci 55(6-7): 932-43 "An update on the mechanisms of action of the peroxisome proliferator-activated receptors (PPARs) and their roles in inflammation and cancer".

George et al. (2004) Neurobiol Dis 16:124-132 "APP intracellular domain is increased and soluble Aβ is reduced with diet-induced hypercholesterolemia in a transgenic mouse model of Alzheimer disease".
Goodman et al. (editors). (1996). The Pharmacological Basis of Therapeutics, 9.sup.th Ed., McGraw-Hill. Table of contents.
Grant (1997) Alz. Dis. Rev. 42-55 "Dietary Links to Alzheimer's Disease".
Greenberg et al. (2000) Arch. Neurol. 57:94-99 "Donepezil Theraphy in Clinical Practice: A Randomized Crossover Study".
Gregg et al. (1986) The Journal of Clinical Investigation, Inc. 78:815-821 "Abnormal in Vivo Metabolism of Apolipoprotein E4 in Humans".
Guillot et al. (1993) Brit. J. of Nutri. 69(2):431-42 "Intestinal absorption and liver uptake of medium-chain fatty acids in non-anaesthetized pigs".
Guzman et al. (2001) Trends in Endocrinology Metabolism 12:169-1733 "Is there an astrocyte-neuron ketone body shuttle?".
Haan and Wallace (2004) Annu Rev Public Health 25:1-24 "Can Dementia Be Prevented? Brain Aging in a Population-Based Context".
Halestrap et al. (1999) J. Biol. Chem. 343:281-299 "The proton-linked monocarboxylate transporter (MCT) family: structure, function and regulation".
Hall et al. (1998) Australian and New Zealand Journal of Psychiatry 32:698-706 "Risk factors and Alzheimer's disease: a comparative study of two communities".
Hamosh (1990) Lingual and Gastric Lipases: Their role in fat digestion. CRCpress, Boca Raton, FL pp. 1-34, 114-116, 127-177.
Hanlon et al. (1995) Atherosclerosis 112:85-90 "Arginine residues at codons 112 and 158 in the apolipoprotein E gene correspond to the ancestral state in humans".
Hasselbalch et al. (1996) Am J Physiol 270:E746-751 "Changes in cerebral blood flow and carbohydrate metabolism during acute hyperketonemia".
Hayes (2000) Am. J. Clin. Nutr. 72(6): 1583-1584 "Medium-chain traicylglycerols may not raise cholesterol".
Henderson (2004) Med Hypotheses 62:689-700 "High carbohydrate diets and Alzheimer's disease".
Hertz et al. (2000) Neurochem Int 37(2-3): 83-102 "Neuronal-astrocytic and cystosolic-mitochondrial metabolite trafficking during brain activation, hyperammonemia and energy deprivation".
Ho et al. (2004) Faseb J 18:902-4 "Diet-induced insulin resistance promotes amyloidosis in a transgenic mouse model of Alzheimer's disease".
Hoyer (1992) Mol Chem Neuropathol 16:207-224 "Oxidative Energy Metabolism in Alzheimer Brain".
Hoyer (1998) J. Neural Transm. 105:415-422 "Is sporadic Alzheimer disease the brain type of non-insulin dependent diabetes mellitus? A challenging hypothesis".
Huff et al. (1987) J. Lipid Res. 28:1118-1123 "Separation and isolation of human apolipoproteins C-II, C-IIIo, C-III1, and C-III2 by chromatofocusing on the Fast Protein Liquid Chromatography System".
Jandacek et al. (1978) Chem. Phys. Lipids 22:163-76 "Physical Properties of Pure Sucrose Octaesters".
Johnson et al. (1999) Int J Epidemiol 28:1102-1109 "Adult nutrient intake as a risk factor for Parkinson's disease".
Jolles et al.(1992) Journal of Neurochemistry 58 (6):2326-2329 "Phosphatidylinositol Kinase Is Reduced in Alzheimer's Disease".
Jong et al. (1999) Arterioscler. Thromb. Vasc. Biol. 19:472-484 "Role of ApoCs in Lipoprotein Metabolism: Functional Differences Between ApoC1, ApoC2, and ApoC3".
Kalmijn et al. (1997) Ann Neurol 42:776-782 "Dietary Fat Intake and the Risk of Incident Dementia in the Rotterdam Study".
Kashiwaya et al. (2000) Proc. Natl. Acad. Sci. USA. 97(10):5440-5444 "D-β-Hydroxybutyrate protects neurons in models of Alzheimer's and Parkinson's disease".
Kimball et al. (2002) J Appl Physiol 93:1168-1680 "Exercise Effects on Muscle Insulin Signaling and Action".
Klivenyi et al. (1999) Nature Medicine 5 (3):347-350 "Neuroprotective effects of creatine in a transfgenic animal model of amyotrophic lateral sclerosis".
Knouff et al. (1999) The Journal of Clinical Investigation 103(11):1579-1586 "Apo E structure determines VLDL clearance and atherosclerosis risk in mice".
Kolanowski et al. (1994) Metabolism 43 (2):180-185 "Stimulatory Influence of D (−) 3-Hydroxybutyrate Feeding on Sympathetic Nervous System Activity in the Rat".
Koo et al. (1999) Proc. Natl. Acad. Sci. 96:9989-9990 "Amyloid diseases: Abnormal protein aggregation in neurodegeneration".
Kudo et al. (1995) J. Biol. Chem. 270:17513-17520 "High Rates of Fatty Acid Oxidation during Reperfusion of Ischemic Hearts Are Associated with a Decrease in Malonyl-CoA Levels Due to an Increase in 5'-AMP-activated Protein Kinase Inhibition of Acetyl-CoA Carboxylase".
Lannert et al. (1998) Behavioral Neuroscience 112 (5):1199-1208 "Intracerebroventricular Administration of Streptozotocin Causes Long-Term Diminutions in Learning and Memory Abilities and in Cerebral Energy Metabolism in Adult Rats".
Lefevre and Aronson (2000) Pediatrics 105:E46 "Ketogenic Diet for the Treatment of Refractory Epilepsy in Children: A Systematic Review of Efficacy".
Leino et al. (2001) Neurochemistry International 38:519-527 "Diet-induced ketosis increases monocarboxylate transporter (MCT1) levels in rat brain".
Ling et al. (2001) J. Med. Chem. 44:3141-3149 "Identification of Alkylidene Hydrazides as Glucagon Receptor Antagonists".
Liu and Barrett (2002) Am J Physiol Endocrinol Metab 283:E1105-1112 "Human protein metabolism: its measurement and regulation".
Loktionov et al. (1999) Atherosclerosis 145:125-135 "Apolipoprotein E and methylenetetrahydrofolate reductase genetic polymiorphisms in relation to other risk factors for cardiovascular disease in UK Caucasians and Black South Africans".
Mahley et al. (1999) J. of Lipid Research 40:1933-49 "Pathogenesis of type III hyperlipoproteinemia (dysbetalipoproteinemia): questions, quandaries, and paradoxes".
Mak et al. (1999) Acta. Paeditr Sin (Medline No. 991412046) 40(2):97-100 "Clinical Experience of Ketogenic Diet on Children With Refractory Epilepsy".
Mattson (1998) Science and Medicine, Mar./Apr. 17-25, Experimental Models of Alzheimer's Disease "Experimental Models of Alzheimer's Disease".
McKhann et al. (1984) Neurology 34:939-943 "Clinical diagnosis of Alzheimer's disease".
Meier-Ruge et al. (1994) Gerontology 40:246-252 "Changes in Brain Glucose Metabolism as a Key to the Pathogenesis of Alzheimer's Disease".
Messier et al. (1996) Behavioural Brain Research 75:1-11 "Glucose regulation and cognitive functions: relation to Alzheimer's disease and diabetes".
Michalik and Van Broeckhoven (2003) Hum Mol Genet 12 Spec No. 2:R173-86 "Pathogenesis of polyglutamine disorders: aggregation revisited".
Mitchell et al. (1995) Clin. Invest. Med. 18:3, 193-216 "Medical aspects of ketone body metabolism".
Moechars et al. (1999) J Biol Chem 274:6483-6492 "Early Phenotypic Changes in Transgenic Mice That Overexpress Different Mutants of Amyloid Precursor Protein in Brain".
Morris et al. (2003) Arch Neurol 60:194-200 "Dietary Fats and the Risk of Incident Alzheimer Disease".
Murray et al. (1999)Harper's Biochemistry 927.
Nadal et al. (2002) Biochem J 366:289-97 "Down-regulation of the mitochondrial 3-hydroxy-3-methylglutaryl-CoA synthase gene by insulin: the role of the forkhead transcription factor FKHRL1".
Nebeling & Lerner (Jun. 1995) J. Am. Diet Assoc. 95(6): 693-697 "Implementing a ketogenic diet based on medium-chain triglyceride oil in pediatric patients with cancer".
Neve et al. (1998) Trends Neurosci 21:15-19 "Alzheimer's disease: a re-examination of the amyloid hypothesis".
Nishimura et al. (1999) Clin. Genes 55:219-225 "Biology of presenilins as causative molecules for Alzheimer disease".
Nordberg Lancet Neurol (2004) 3:519-27 "PET imaging of amyloid in Alzheimer's disease".

Odle, J. (1997) J Nutr. 127:1061-1067 "New Insights into the Utilization of Medium-Chain Triglycerides by the Neonate: Observations from a Piglet Model".

Ogawa et al. (1996) J. of the Neurological Sciences 139:78-82 "Altered energy metabolism in Alzheimer's disease".

Osuntokun et al. (1995) Ann Neurol 38:463-465 "Lack of an Association Between Apolipoprotein E E4 and Alzheimer's Disease in Elderly Nigerians".

Pegorier et al. (1988) Biochem Journal 249:801-806, "Fatty acid metabolism in hepatocytes isolates from rats adapted to high-fat diets containing long-or medium-chain triacylglycerols".

Pettegrew et al. (2000) Molecular Psychiatry 5: 616-632 "Acetyl-L-carnitine physical-chemical, metabolic, and therapeutic properties; relevance for its mode of action in Alzheimer's disease and geriatric depression".

Poirier et al. (1995) Proc. Natl. Acad. Sci. 92:12260-12264 "Apolipoprotein E4 allele as a predictor of cholinergic deficits and treatment outcome in Alzheimer disease".

Qureshi et al. (2000) J. Biol. Chem. 275:36590-36595 "Activation of Insulin Signal Transduction Pathway and Anti-diabetic Activity of Small Molecule Insulin Receptor Activators".

Refolo et al. (2000) Neurobiol Dis 7:321-331 "Hypercholesterolemia Accelerates the Alzheimer's Amyloid Pathology in a Transgenic Mouse Model".

Reger (2003) Neurobiol of Aging 25:311 "Effects of β-hydroxybutyrate on cognition in memory-impaired adults".

Reiman et al. (1996) N Engl J Med 334:752-758 "Preclinical Evidence of Alzheimer's Disease in Persons Homozygous for the E4 Allele for Apolipoprotein E".

Robinson et al. (2004) Neurobiol Aging 25:609-15 "Lessons from the AN 1792 Alzheimer vaccine: lest we forget".

Roheim et al. (1979) Proc Natl Acad Sci U S A 76:4646-4649 "Apolipoproteins in human cerebrospinal fluid".

Sato et al. (2003) Exp Biol Med (Maywood) 228:1208-12 "Physical Exercise Improves Glucose Metabolism in Lifestyle-Related Diseases".

Schenk et al. (1999) Nature 400:173-7 "Immunization with amyloid-β attenuates Alzheimer-disease-like pathology in the PDAPP mouse".

Schoonjans et al. (1999) FEBS Lett 452(3): 160-4 "3-Hydroxy-3-methylglutaryl CoA reductase inhibitors reduce serum triglyceride levels through modulation of apolipoprotein C-III and lipoprotein lipase".

Selkoe et al. (1999) Nature 399: A23-31 "Translating cell biology into therapeutic advances in Alzheimer's disease".

Selkoe (2001) Physiol Rev 81(2): 741-66 "Alzheimer's Disease: Genes, Proteins, and Therapy".

Selkoe (2004) Ann Intern Med 140:627-38 "Alzheimer Disease: Mechanistic Understanding Predicts Novel Therapies".

Selkoe, D. J. (1994) J. Neuropathol. Exp. Neurol. 53:438-447 "Alzheimer's Disease: A Central Role for Amyloid".

Shah et al. (2000) Am J Physiol Endocrinol Metab 279:E715-29 "4E-BP1 and S6K15:01 PM translational integration sites for nutritional and hormonal information in muscle".

Shi et al. (1999) J. Biol. Chem. 274: 9421-9426 "A Single Aminio Acid Change (Substitution of Glutamate 3 with Alanine) in the N-terminal Region of Rat Liver Carnitine Palmitoyltransferase I Abolishes Malonyl-CoA Inhibition and High Affinity Binding".

Shie et al. (2002) Neuroreport 13:455-9 "Diet-induced hypercholesterolemia enhances brain A beta accumulation in transgenic mice".

Simpson et al. (1994) Ann Neurol 36:800-801 "Reduced Glucose Transporter Concentrations in Brains of Patients with Alzheimer's Disease".

Sirven, et al. (Dec. 1999) Epilepsia 40(12): 1721-1726 "The Ketogenic Diet for Intractable Epilepsy in Adults: Preliminary Results".

Staels et al. (1998) Circulation 98(19): 2088-93 "Mechanism of Action of Fibrates on Lipid and Lipoprotein Metabolism".

Stokin et al. (2005) Science 307:1282-8 "Axonopathy and Transport Deficits Early in the Pathogenesis of Alzheimer's Disease".

Strittmatter et al. (1996) Annu. Rev. Neurosci. 19:53-77 "Apolipoprotein E and Alzheimer's Disease".

Sugiura et al. (1996) 229:58-64 "2-Arachidonoylglycerol, a Putative Endogenous Cannabinoid Receptor Ligand, Induces Rapid, Transient Elevation of Intracellular Free Ca2+ in Neuroblastoma X Glioma Hybrid NG108-15 Cells".

Sugiura et al. (1997) J. Biol. Chem. 122:890-895 "Is the Cannabinoid CB1 Receptor a 2-Arachidonoylglycerol Receptor? Structural Requirements for Triggering a Ca2+ Transient in NG108-15 Cells".

Sugiura et al. (2000) J. Biol. Chem. 275:605-612 "Evidence That 2-Arachidonoylglycerol but Not N-Palmitoylethanolamine or Anandamide Is the Physiological Ligand for the Cannabinoid CB2 Receptor".

Sugiura, et al. (1999) J. Biol. Chem. 274:2794-2801 "Evidence That the Cannabinoid CB1 Receptor Is a 2-Arachidonoylglycerol Receptor".

Swaab et al. (1998) Prog Brain Res 117:343-377 "Reduced neuronal activity and reactivation in Alzheimer's disease".

Takada et al. (1991) Bull. Inst. Chem. Res., 69:77-83 "Preparation of Cellobiose Octa(n-alkanoate)s and Their Thermal Properties".

Takada et al. (1992) Liq. Cryst. 12:337-45 "Columnar liquid crystals in oligosaccharide derivatives".

Takada et al. (1995) Liq. Cryst. 19:441-8 "Discotic columnar liquid crystals in oligosaccharide derivatives".

Taylor et al. (2002) Science 296:1991-5 "Toxic Proteins in Neurodegenerative Disease".

Thal et al. (1996) Neurology 47(3):705-711 "A 1-year multicenter placebo-controlled study of acetyl-L-carnitine in patients with Alzheimer's disease".

Thavendiranathan, et. al. (2000) Exp Neurol 161(2): 696-703 "The MCT Ketogenic Diet: Effects on Animal Seizure Models".

Van Wymlbeke (2001) Am. J. Clin. Nut. 74:620 "Substrate oxidation and control of food intake in men after a fat-substitute meal compared with meals supplemented with an isoenergetic load of carbohydrate, long-chain triacylglycerols, or medium-chain triacylglycerols".

Veech et al. (2001) IUBMB Life 51(4):241-247 "Ketone Bodies, Potential Therapeutic Uses".

Veneman et al. (1994) Diabetes 43:1311-1317 "Effect of Hyperketonemia and Hyperlacticacidemia on Symptoms, Cognitive Dysfunction, and Counterregulatory Hormone Responses During Hypoglycemia in Normal Humans".

Wang et al. (2005) Faseb J 19:659-661 "Caloric restriction attenuates β-amyloid neuropathology in a mouse model of Alzheimer's disease".

Wang et al. (2000) J. Biol. Chem. 275:20782-20786 "Abnormal Sodium Stimulation of Carnitine Transport in Primary Carnitine Deficiency".

Winocur and Greenwood (1999) Behav Brain Res 101:153-61 "The effects of high fat diets and environmental influences on cognitive performance in rats".

Witters et. al. (1988) Proc. Natl. Acad. Sci. USA 85:5473-5477 "Insulin stimulates the dephosphorylation and activation of acetyl-CoA carboxylase".

Wu et al. (2003) Neuroscience 119:365-75 "A Saturated-Fat Diet Aggravates the Outcome of Traumatic Brain Injury on Hippocampal Plasticity and Cognitive Function by Reducing Brain-Derived Neurotrophic Factor".

Yamamoto et al. 2000 Cell 101:57-66 "Reversal of Neuropathology and Motor Dysfunction in a Conditional Model of Huntington's Disease".

York et al. (1997) Carb. Research 300(3):199-206 "Determination of the absolute configuration of monosaccharides by $^1$H NMR spectroscopy of their per-0-(S)-2-methylbutyrate derivatives".

Zekraoui et al. (1997) Hum Biol 69:575-581 "High frequency of the apolipoprotein E 4 allele in African pygmies and most of the African populations in Sub-Saharan Africa".

Zhao et al. (2004) Pediatr Res 55:498-506 "Detrimental Effects of the Ketogenic Diet on Cognitive Function in Rats".

Zhou et al. (1998) Molecular Endocrinology 12:1594-1604 "Nuclear Receptors Have Distinct Affinities for Coactivators: Characterization by Fluorescence Resonance Energy Transfer".

Zief (1950) J. of Amer. Chem. Soc. 72:1137-40 "Unsaturated esters of sucrose".

Zubenko et al. (1999) Biol Psychiatry 45:731-736 "Reductions in Brain Phosphatidylinositol Kinase Activities in Alzheimer's Disease".

International Search Report, prepared for international patent application PCT/US09/49605 by the U.S. Patent and Trademark Office as International Searching Authority, mailed Aug. 14, 2009, 2 pages.

Extended European Search Report, prepared for European Application No. 07797196.8 by the European Patent Office, dated Aug. 24, 2009, 5 pages.

Crook et al. (1986) Developmental Neuropsychology 2(4):261-276, "Age-associated memory impairment: proposed diagnostic criteria and measures of clinical change—report of a national institute of mental health work group".

DeCarli (2003) The Lancet Neurology 2:15-21, "Mild cognitive impairment: prevalence, prognosis, aetiology, and treatment".

Fratiglioni et al (1991) Neurology 1:1886-1992, "Prevalence of Alzheimer's disease and other dementias in an elderly urban population: Relationship with age, sex, and education;" Downloaded from www.neurology.org on Oct. 15, 2010.

Hänninen (1996) University of Kuopio, Department of Neurology; Doctoral Dissertation, "Age-associated memory impairment: a neuropsychological and epidemiological study".

Jankovic et al (2008) Neuropsychiatric Disease and Treatment 4(4):743-757, "Current approaches to the treatment of parkinson's disease".

Kidd (2008) Alternative Medicine Review 13(2):85-115, "Alzheimer's disease, amnestic mild cognitive impairment, and age-associated memory impairment: current understanding and progress toward integrative prevention".

Loveman et al (2006) Health Technology Assessment 10(1):1-375, "The clinical and cost-effectiveness of donepezil, rivastigmine, galantamine and memantine for Alzheimer's disease".

Rocca et al. (1991) Annals of Neurology 30(3):381-390, "Frequency and distribution of alzheimer's disease in europe: a collaborative study of 1980-1990 prevalence findings".

Kashiwaya et al. (2000) PNAS, 97(10):5440-5444, "D-beta-hydroxybutyrate prospects neurons in models of Alzheimer's and Parkinson's disease".

Freeman et al. (2006) Epilepsy Research 68:145-180, "The ketogenic diet: From molecular mechanisms to clinical effects".

Zhao et al. (2004) Pediatric Research 55(3):498-506, "Detrimental Effects of the Ketogenic Diet on Cognitive Function in Rats".

Introducing Neurontin Capsules in a New Shape Ad (1996), 1 page.

* cited by examiner

USE OF KETOGENIC COMPOUNDS FOR TREATMENT OF AGE-ASSOCIATED MEMORY IMPAIRMENT

RELATED APPLICATIONS

This application is a 35 U.S.C. §371 national phase application of PCT/US07/65873 (WO 2007/115282), filed on Apr. 3, 2007 entitled "Use of Ketogenic Compounds for Treatment of Age-Associated Memory Impairment," which application claims the benefit of U.S. Provisional Application Serial No. 60/744,140 filed Apr. 3, 2006 entitled "Use of Medium Chain Triglycerides for the Treatment and Prevention of Age-Associated Memory Impairment," which are incorporated herein by reference in their entirety; this application is also a continuation-in-part of pending U.S. patent application Ser. No. 11/021,920, filed on Dec. 22, 2004, entitled "Use of Medium Chain Triglycerides for the Treatment and Prevention of Alzheimer's Disease and Other Diseases Resulting from Reduced Neuronal Metabolism II," which application is a continuation of U.S. patent application Ser. No. 10/152,147, filed on May 20, 2002 (now U.S. Pat. No. 6,835,750), entitled "Use of Medium Chain Triglycerides for the Treatment and Prevention of Alzheimer's Disease and Other Diseases Resulting from Reduced Neuronal Metabolism II", which application is a continuation-in-part of U.S. patent application Ser. No. 09/845,741, filed on May 1, 2001, entitled "Use of Medium Chain Triglycerides for the Treatment and Prevention of Alzheimer's Disease and Other Diseases Resulting from Reduced Neuronal Metabolism," which application is a nonprovisional of U.S. Provisional Application No. 60/200,980, filed on May 1, 2000, entitled "Use of Medium Chain Triglycerides for the Treatment and Prevention of Alzheimer's Disease and Other Diseases Resulting from Reduced Neuronal Metabolism," all of which are incorporated herein by reference in their entirety for all that they teach and disclose.

BACKGROUND OF THE INVENTION

Aging causes deterioration of various aspects of physiology in normal adults, including memory performance. Such age related declines in cognitive performance have long been recognized by medical practitioners. Plato and Aristotle (384-322 BC) both wrote about the declines in mental performance with age, and how this should be used to exclude aged individuals from certain jobs: "there is not much left of the acumen of the mind which helped them in their youth, nor of the faculties which served the intellect, and which some call judgment, imagination, power of reasoning and memory. They see them gradually blunted by deterioration and see that they can hardly fulfill their function."

In more recent times, mental decline has been quantified by a series of cognitive tests and is now a well accepted phenomenon. Impairment of memory performance in the elderly has been detected in several standard memory tests, including the Wechsler Memory Scale (WMS) and immediate and delayed Visual Reproduction Test (Trahan et al. Neuropsychology, 1988 19(3) p. 173-89), the Rey Auditory Verbal Learning Test (RAVLT) (Ivnik, R. J. et al. Psychological Assessment: A Journal of Consulting and Clinical Psychology, 1990 (2): p. 304-312) and others (for review see Larrabee and Crook, Int. Psychogeriatr, 1994 6(1): p. 95-104.

To characterize memory loss more systematically, the National Institute of Mental Health (NIMH) created a work group which proposed a criteria for "age-associated memory impairment" (AAMI) (Crook T. H. et al. Dev. Neuropsychol, 1986, 2: p. 261-276.) The criteria for AAMI include, complaints of memory loss in persons over the age of 50 years, impairment on a standardized memory test compared to young adults, and absence of dementia or any medical condition that could produce cognitive deterioration. Because AAMI is related to "normal" aging and not a pathological condition the prevalence is expected to be high and increase with increasing age. Recent estimates vary from 18% to 85%, depending on the subjects' age and the population studied.

The clinical course and causes of AAMI are poorly understood. Since AAMI is a part of aging it has frequently been attributed to the general deterioration of the body due to cellular damage. Age related increases in cellular damage are often ascribed to oxidative damage from a variety of sources. Despite being part of normal aging, several possible treatments strategies have been attempted to alleviate AAMI and have met with some success. For example, phosphatidylserine has shown some efficacy in AAMI trials.

The human brain is one of the most metabolically active organs in the body and requires large amounts of energy for proper function. Cerebral oxygen consumption for an average adult human is roughly 3.5 ml/100 g/min. For an average sized brain of 1,400 grams, this is about 40 ml $O_2$/min. At rest the average person will use ~250 ml $O_2$/min. Therefore the brain uses approximately 16 percent of the total $O_2$ consumed. This is remarkable in that the brain accounts for only about 2 percent of the total body mass. Most of the oxygen in the brain is used for the oxidation of glucose. Under normal conditions glucose is primary fuel for the brain while the contribution of fatty acids is considered minor. The average adult brain consumes approximately 110 grams of glucose a day. The dependence on glucose puts the brain at risk if circulating glucose levels drop, such that sudden bouts of hypoglycemia cause impairment of cognitive function. For example, if large amounts of insulin are injected this will cause a sudden drop in blood glucose and cognitive dysfunction, including memory problems, sensory disturbances and even coma.

However under certain conditions when glucose levels are limiting, such as neonatal development or starvation, the liver will mobilize ketone bodies as a supplemental fuel for the body, and in particular cerebral neurons. Ketone bodies (β-hydroxybutyrate, acetoacetate and acetone) are derived from the incomplete oxidation of fatty acids by both hepatocytes and glial cells, and released into the bloodstream to provide a supplement to glucose. Ketone bodies cannot fully substitute for glucose, but can account for a significant fraction of cerebral metabolism. In early studies conducted on fasting of obese human subjects, considerable uptake of ketone bodies into the brain was observed. The uptake was sufficiently large to account for almost 50% of total cerebral $O_2$ usage.

The ability of ketone bodies to supplement glucose in the brain has been used to treat conditions of low glucose availability to the brain. GLUT1 is a constitutive glucose transporter that transports glucose into the central nervous system (CNS). The high glucose requirement of the brain requires that two functional copies of the GLUT1 gene be present. If one copy of GLUT1 is non-functional this results in GLUT1 deficiency syndrome. The resulting low glucose levels during development lead to infant seizures, delayed development and microcephaly. Partial relief of these symptoms can be achieved by increasing serum ketone levels by administration of a ketogenic diet. Thus, if glucose uptake or use is limited, ketone bodies may serve to supplement energy requirements.

One physiological hallmark of aging in mammals is a decreased uptake and metabolism of glucose within the brain.

The impaired glucose metabolism in the brain may contribute or exacerbate the cognitive deficits observed during normal aging. Facilitation of memory in elderly subjects occurs when glucose levels are elevated by the administration of carbohydrate. However, such a treatment poses challenges since elevated blood glucose levels are difficult to maintain and must be within a relatively narrow window, as excessive hyperglycemia is associated with cognitive impairments. Therefore it is important to explore other aspects of the model.

Substantial scientific evidence has shown that defects in cerebral glucose metabolism occur during aging in several mammalian species. A series of studies done in the 1980s demonstrated decreased cerebral glucose metabolism in aged rats. One study examined the role that the decreased metabolic rate played in the cognitive decline of aging rats. Aged (22-24 months) and young (3 month) rats were tested in a series of behavioral tests including: water maze test (spatial learning), time on a round bridge (motor coordination), open field test (spontaneous activity) and the startle response. Cerebral glucose utilization was also examined in these same rats. As a group, aged animals demonstrated lowered regional glucose utilization when compared with the younger animals. The aged group also showed large heterogeneity in extent and regions of decreased glucose metabolism. Interestingly, the amount of decreased regional glucose metabolism correlated with impairment in cognitive tests. For example, declines in glucose use in the prefrontal cortex correlated well with spatial learning impairment. Similar decreases in glucose metabolism have been observed in rhesus monkeys and dogs.

Early studies in humans using positron emission tomography failed to find evidence of decreased cerebral glucose metabolism in normal aged subjects. However, more recent studies employing more sensitive techniques and instrumentation have found that regional decreases in glucose metabolism are associated with normal human aging. In a study of 25 healthy volunteers between the ages of 20 to 68, total oxygen consumption in the brain was found to be reduced approximately 6% per decade. Importantly, the decline still was evident when cortical atrophy was included in the calculations, demonstrating that the decreases in metabolism are not simply due to cell loss. Others have mapped the decreases in metabolism to specific regions of the brain to create a "metabolic topography of normal aging". This map located metabolic decline to largely frontal regions of the brain and represented an approximately 12% decrease in global metabolic rate between the ages of 20 and 80.

Attempts to improve memory performance in the elderly by increasing glucose availability have met with some success in both animal models and in humans. For example, in a Y maze test, both young and old mice normally enter the new arm if there is no delay when the animals are placed in the maze. This is a measure of spontaneous alteration. If, however, a delay of 1 minute is used, young mice (2 month) still perform well on this task but old mice (2 year) do not. Yet, if the mice are given glucose before the test, the old mice perform as well as the young mice, and there is no increase in the ability of the young mice (Stone, W. S., et al., Glucose attenuation of deficits in spontaneous alternation behavior and augmentation of relative brain 2-deoxyglucose uptake in old and scopolamine-treated mice, *Psychobiology*, 1992, 20:270-279). This is consistent with studies in humans that have largely shown increases in cognition following glucose administration in elderly groups but not for young groups. In one study, two sets of subjects, one young (mean age 20 years old) and one elderly (mean age 67 years old) were given either a sugar free lemon drink sweetened with artificial sweeteners (0 g carbohydrates) or a drink sweetened with sugar (50 g carbohydrate) on alternate visits in a crossover design. On each visit the subjects were given a series of cognitive tests, including a paired association task, a test of contextual memory, a test of immediate recall, and a test of visual memory. The glucose improved the scores of the elderly group but not the young group. Such experiments have been replicated several times and seem to indicate that memory facilitation by glucose is characterized by an inverted-U shape, with too much glucose negating the effect.

The mechanism for increased memory after glucose administration is still unclear but may be related to increased energy production and the corresponding increased acetylcholine production. Yet, glucose may not be a practical means to elevate memory in the aged for several reasons. (1) Elevated glucose levels are difficult to maintain in a healthy mammal. (2) Hyperglycemia may improve memory but may prove detrimental to other organ systems. (3) Elevated blood glucose may lead to chronically elevated insulin levels and the problems associated with hyperinsulinemia.

Interestingly other substrates may also facilitate memory in aged animals. For example, morphine is known to impair memory formation yet this effect can be blocked by co-administering glucose. Similarly pyruvate can also block the effects of morphine administration.

There has been long experience with ketogenic diets, which mimic starvation, in children treated for epilepsy. The diet is a medical therapy and should be used under the careful supervision of a physician and/or dietician. The diet carefully controls caloric input and requires that the child eat only what has been included in the calculations to provide 90% of the day's calories as fats. However, such diets are generally unsuitable for use in adults due to: (1) adverse effects on the circulatory system from incorporation of cholesterol and long chain triglycerides as the primary fat in these diets; (2) poor patient compliance due to the unappealing nature of the low carbohydrate diet.

The prior art provides descriptions of ketogenic diets in which fat is high and carbohydrates are limited. In summary, the rationale of such diets is that intake of high amounts of fat, whether long-chain or medium-chain triglycerides can increase blood ketone levels in the context of a highly-regimented diet in which carbohydrate levels are absent or limited. Limitation of carbohydrate and insulin are believed to prevent re-esterification in adipose tissue. Although the ketogenic diet has been known for decades, there does not appear to be any prior art teaching or suggesting that MCT therapy be used to treat diseases of reduced neuronal metabolism in patients with any age-associated cognitive decline, such as AAMI, and the like.

There is thus a need in the art to develop compositions and methods for the treatment and/or prevention of cognitive impairment, particularly in aging or geriatric mammals such as humans.

Various publications, including patents, published applications, technical articles and scholarly articles are cited throughout the specification. Each of these cited publications is incorporated by reference herein, in its entirety. Full citations for publications not cited fully within the specification are set forth at the end of the specification.

SUMMARY OF THE INVENTION

In one embodiment, the present invention includes compositions compounds capable of elevating ketone bodies in a mammal, such as, for example, medium chain triglycerides (MCT), including a nutritional drink for oral consumption comprising: a unit dose sufficient to a) raise blood levels of D-β-hydroxybutyrate to about 0.1 to about 5 mM or b) raise urinary excretion levels of D-β-hydroxybutyrate to about 5 mg/dL to about 160 mg/dL; L-carnitine, a plurality of vitamins; flavoring, and a carbohydrate source and wherein the MCT, if included, are of the formula:

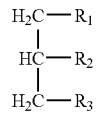

wherein the R1, R2, and R3 esterified to the glycerol backbone are each independently fatty acids having carbon chains of 5-12 carbons.

In another embodiment, the present invention includes a method of treatment for Age-Associated Memory Impairment (AAMI), comprising the steps of identifying a mammal having, or at risk of AAMI; and administering to the mammal a composition comprising at least one compound capable of elevating ketone body concentrations in an amount effective for the treatment of or prevention of loss of cognitive function caused by reduced neuronal metabolism in AAMI.

The present invention also relates to a method for treatment of age related cognitive decline or AAMI, comprising the steps of identifying a population of healthy aging mammals having AAMI, dividing the population into at least a control group and one or more test groups, formulating at least one delivery system for delivering a composition comprising at least one compound capable of elevating ketone body concentrations in an amount effective for elevating at least one type of ketone body in the blood of an individual mammal, wherein, on an extended regular basis, each test group receives a formulation delivering a composition comprising at least one compound capable of elevating ketone body concentrations and the control group does not receive any composition comprising at least one compound capable of elevating ketone body concentrations. The method further comprises comparing at least one neuropsychological test result in the control and test groups, determining which of the delivery systems for delivering the composition comprising at least one compound capable of elevating ketone body concentrations was effective in improving the results of at least one neuropsychological test; and administering a treatment-based delivery system determined in the previous step to a population of aging mammals, thereby treating AAMI.

DETAILED DESCRIPTION OF THE INVENTION

Figure 1:
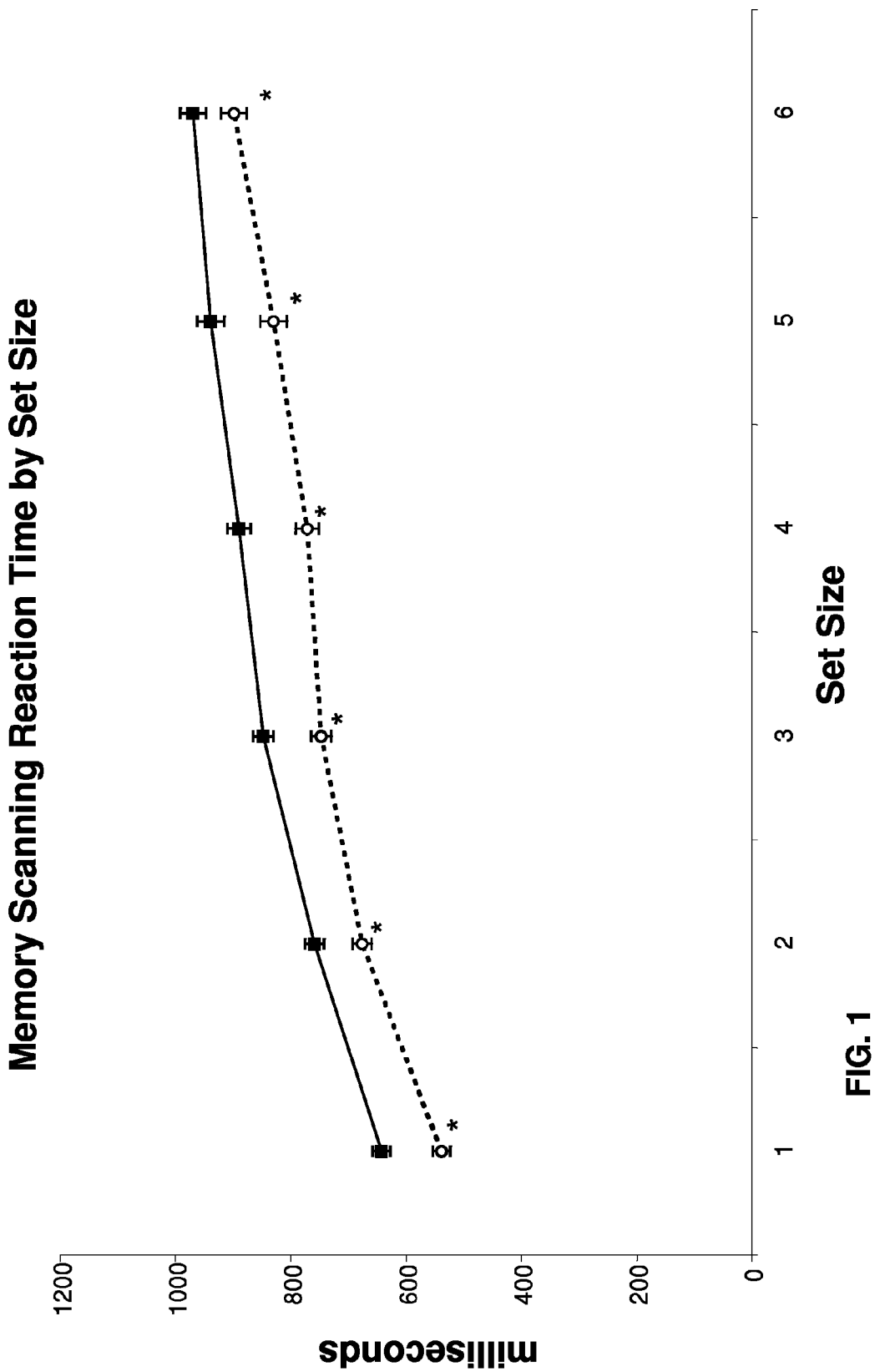
FIG. 1 shows the improvement of mental performance, as measured by the improvements in Memory Scanning Reaction Time for all set sizes for an AAMI cohort.

It is the novel insight of this invention that compositions comprising at least one compound capable of elevating ketone body concentrations, such as, for example, medium chain triglycerides (MCT) and or medium chain fatty acids (MCFA), are useful as a treatment and preventative measure in patients with any age-associated cognitive decline, such as AAMI, and the like. These conditions are associated with reduced neuronal metabolism. As used herein, reduced neuronal metabolism refers to all possible mechanisms that could lead to a reduction in neuronal metabolism. Such mechanisms include, but are not limited to mitochondrial dysfunction, free radical attack, generation of reactive oxygen species (ROS), ROS-induced neuronal apoptosis, defective glucose transport or glycolysis, imbalance in membrane ionic potential, dysfunction in calcium flux, and the like.

In light of the deficiencies for other methods to treat deficits of energy metabolism in the brain, discussed hereinabove, the present invention contemplates use of another substance to improve memory performance, in particular, ketone bodies, which is known to be readily utilized by the brain.

Ketone bodies, in particular β-hydroxybutyrate (βHB) and acetoacetate serve a critical role in the development and health of cerebral neurons. Numerous studies have shown that the preferred substrates for the developing mammalian neonatal brain are ketone bodies. There is a large body of evidence demonstrating that ketone bodies are used in a concentration dependent manner by the adult human brain, even in the elderly. Ketone bodies (KB) offer several advantages to glucose for memory facilitation in the elderly. (1) KB can be artificially elevated by the administration of large amounts of medium chain triglycerides (MCT) without altering glucose levels. (2) Hyperketonemia can be induced and sustained for many hours. (3) KB readily cross the blood brain barrier. (4) KB are readily metabolized by cerebral neurons and can be used to generate ATP and acetylcholine. In particular, a composition developed by the inventors, Ketasyn™, provides a simple and safe method to induce hyperketonemia.

The active ingredient of Ketasyn™ is MCT. MCT are comprised of fatty acids with chain length between 5-12 carbons and have been researched extensively. MCT are metabolized differently from the more common Long Chain Triglycerides (LCT). In particular, when compared to LCT, MCT are more readily digested to release medium chain fatty acids (MCFA) which exhibit increased rates of portal absorption, and undergo obligate oxidation. MCFA have melting points much lower than long chain fatty acids (LCFA), and therefore the MCFA and corresponding MCT are liquid at room temperature. MCFA are smaller and more ionized at physiological pH compared to LCFA, and hence MCFA are much more soluble in aqueous solutions. The small size and decreased hydrophobicity of MCT increases the rate of digestion and absorption relative to LCT.

When ingested, MCT are first processed by lipases, which cleave the fatty acid chains from the glycerol backbone. Some lipases in the pre-duodenum preferentially hydrolyze MCT over LCT and the released MCFA are then partly absorbed directly by the stomach mucosa. Those MCFA which are not absorbed in the stomach are absorbed directly into the portal vein and not packaged into lipoproteins. LCFA derived from normal dietary fat are re-esterified into LCT and packaged into chylomicrons for transport in the lymph. This greatly slows the metabolism of LCT relative to MCT. Since blood transports much more rapidly than lymph, MCFA quickly arrive at the liver.

In the liver MCFA undergo obligate oxidation. In the fed state LCFA undergo little oxidation in the liver, due mainly to the inhibitory effects of malonyl-CoA. When conditions favor fat storage, malonyl-CoA is produced as an intermediate in lipogenesis. Malonyl-CoA allosterically inhibits carnitine palmitoyltransferase I, and thereby inhibits LCFA transport into the mitochondria. This feedback mechanism prevents futile cycles of lipolysis and lipogenesis. MCFA are, to a large extent, immune to the regulations that control the oxidation of LCFA. MCFA enter the mitochondria without the use of carnitine palmitoyltransferase I, therefore MCFA by-pass this regulatory step and are oxidized regardless of the metabolic state of the organism. Importantly, since MCFA enter the liver rapidly and are quickly oxidized, large amounts of ketone bodies are readily produced from MCFA and a large oral dose of MCT (roughly 20 mL) will result in sustained hyperketonemia. It is the novel insight of the inventor that MCT may be administered outside of the context of a ketogenic diet. Therefore, in the present invention carbohydrates may be consumed at the same time as MCT. This represents a significant advantage over the prior art, which only describes the use of MCT in the context of a ketogenic diet. Such diets greatly restrict both carbohydrate and protein in the diet and are, in practice, extremely difficult for patients to comply with. The present invention represents a significant advantage over ketogenic diet prior art, in that in the present invention the subject is free follow any diet and does not have to adhere to any dietary restrictions.

According to the present invention, high blood ketone levels will provide an energy source for brain cells that have compromised glucose metabolism, via the rapid oxidation of MCFA to ketone bodies, leading to improved performance in, and/or reversal, prevention, reduction, and/or delaying of decline in one or more of cognitive function, memory, motor performance, cerebrovascular function, and/or behavior. As used herein, "patient" refers to any mammal, including humans that may benefit from treatment of disease and conditions resulting from reduced neuronal metabolism.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The background of this invention supports the present invention in the following ways. (1) Neurons of the brain can use both glucose and ketone bodies for respiration. (2) The neurons of patients with age-associated cognitive decline, such as AAMI, may have defects in glucose metabolism. (3) Aging may cause defects in metabolism that may underlie susceptibility to any age-associated cognitive decline, such as AAMI, and the like. Hence, supplementation of patients with any age-associated cognitive decline, such as AAMI, and the like with MCT will restore neuronal metabolism.

In one embodiment, a compound capable of elevating a ketone body concentrations in the body of a mammal include "medium chain triglycerides" or "MCT", referring to any glycerol molecule ester-linked to three fatty acid molecules, each fatty acid molecule having a carbon chain of 5-12 carbons. MCT may be represented by the following general formula:

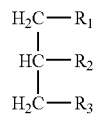

where R1, R2 and R3 are fatty acids having 5-12 carbons in the carbon backbone esterified to the a glycerol backbone. The structured lipids of this invention may be prepared by any process known in the art, such as direct esterification, rearrangement, fractionation, transesterification, or the like. For example, the lipids may be prepared by the rearrangement of a vegetable oil such as coconut oil. The length and distribution of the chain length may vary depending on the source oil. For example, MCT containing 1-10% C6, 30-60% C8, 30-60% C10, 1-10% C10 are commonly derived from palm and coconut oils. MCT containing greater than about 95% C8 at R1, R2 and R3 can be made by semi-synthetic esterification of octanoic acid to glycerin. Such MCT behave similarly and are encompassed within the term MCT as used herein.

"Effective amount" refers to an amount of a compound, material, or composition, as described herein that is effective to achieve a particular biological result. Such results include, but are not limited to, at least one of the following: enhancing cognitive function, improving memory, improving liver function, increasing daytime activity, improving learning, improving attention, improving social behavior, improving motor performance, and/or improving cerebrovascular function, particularly in aging or geriatric mammals. In various embodiments, "effective amount" refers to an amount suitable to reverse, reduce, prevent, or delay a decline in the above qualities, for example, cognitive function or performance, memory, learning rate or ability, problem solving ability, attention span and ability to focus on a task or problem, motor function or performance, social behavior, and the like. Preferably the reversal, prevention, reduction, or delay of a decline in an individual or population is relative to a cohort— e.g. a control mammal or a cohort population that has not received the treatment. Such effective activity may be achieved, for example, by administering the compositions of the present invention to a mammal or to a population of mammals.

Effectiveness for treatment of the aforementioned conditions may be assessed by improved results from at least one neuropsychological test. These neuropsychological tests are known in the art and include Clinical Global Impression of Change (CGIC), Rey Auditory Verbal Learning Test (RAVLT), First-Last Names Association Test (FLN), Telephone Dialing Test (TDT), Memory Assessment Clinics Self-Rating Scale (MAC-S), Symbol Digit Coding (SDC), SDC Delayed Recall Task (DRT), Divided Attention Test (DAT), Visual Sequence Comparison (VSC), DAT Dual Task (DAT Dual), and Geriatric Depression Scale (GDS), among others.

The term "cognitive function" s refers to the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness. "Enhanced cognitive function" or "improved cognitive function" refers to any improvement in the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness, as measured by any means suitable in the art.

"Behavior" is used herein in a broad sense, and refers to anything that a mammal does in response or reaction to a given stimulation or set of conditions. "Enhanced behavior" or "improved behavior" refers to any improvement in anything that a mammal does in response or reaction to a given stimulation or set of conditions.

"Decline" of any of the foregoing categories or specific types of qualities or functions in an individual (characteristics or phenotypes) is generally the opposite of an improvement or enhancement in the quality or function. An "effective amount" (as discussed above) of a composition may be an amount required to prevent decline altogether or to substantially prevent decline ("prevent" decline), to reduce the extent or rate of decline ("reduce" decline), or delay the onset or progression of a decline ("delay" a decline), or lead to an improvement from a previous decline ("reversal of" or "reversing" a decline). Prevention, reduction, or delay of "decline" is frequently a more useful comparative basis when working with non-diseased aging mammals. Reversal, prevention, reduction, and delay can be considered relative to a control or cohort which does not receive the treatment, for example, the composition of interest. Reversal, prevention, reduction, or delay of either the onset of a detrimental quality or condition, or of the rate of decline in a particular function can be measured and considered on an individual basis, or in some embodiments on a population basis. The net effect of reversing, preventing, reducing, or delaying decline is to have less decrease in memory, cognitive, motor, or behavioral functioning per unit time, or at a given end point. In other words, ideally, for an individual or in a population, cognitive, motor, and behavioral functioning is maintained at the highest possible level for the longest possible time. For purposes herein, an individual can be compared to a control individual, group, or population. A population can likewise be compared to an actual individual, to normalized measurements for an individual, or to a group or population as is useful.

"Aging" as used herein means being of advanced age, such that the mammal has exceeded 50% of the average lifespan for its particular species. Aging mammals are sometimes referred to herein as "aged" or "geriatric" or "elderly." Healthy aging mammals are those with no known diseases, particularly diseases relating to loss of cognitive function such as might confound the results. In studies using healthy aging mammals, cohort mammals are preferably also healthy aging mammals, although other healthy mammals with suitable memory, cognitive, motor, or behavioral functioning may be suitable for use as comparative specimens. If mammals with specific disease diagnoses, or memory, cognitive, motor, or behavioral limitations are used, then the cohort mammals should include mammals that are similarly diagnosed, or which present with similar indicia of the disease or memory, cognitive, motor, or behavioral limitation.

Administration can be on an as-needed or as-desired basis, for example, once-monthly, once-weekly, daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the mammal or otherwise contacted with or admixed with daily feed or food. When utilized as a daily feed or food, administration will be well known to those of ordinary skill.

Administration can also be carried out on a regular basis, for example, as part of a treatment regimen in the mammal. A treatment regimen may comprise causing the regular ingestion by the mammal of an inventive composition in an amount effective to enhance cognitive function, memory, and behavior in the mammal. Regular ingestion can be once a day, or two, three, four, or more times per day, on a daily or weekly basis. Similarly, regular administration can be every other day or week, every third day or week, every fourth day or week, every fifth day or week, or every sixth day or week, and in such a regimen, administration can be multiple times per day. The goal of regular administration is to provide the mammal with optimal dose of an inventive composition, as exemplified herein.

The compositions provided herein are, in one embodiment, intended for "long term" consumption, sometimes referred to herein as for 'extended' periods. "Long term" administration as used herein generally refers to periods in excess of one month. Periods of longer than two, three, or four months comprise one embodiment of the instant invention. Also included are embodiments comprising more extended periods that include longer than 5, 6, 7, 8, 9, or 10 months. Periods in excess of 11 months or 1 year are also included. Longer terms use extending over 1, 2, 3 or more years are also contemplated herein. In the case of certain aging mammals, it is envisioned that the mammal would continue consuming the compositions for the remainder of its life on a regular basis. "Regular basis" as used herein refers to at least weekly, dosing with or consumption of the compositions. More frequent dosing or consumption, such as twice or thrice weekly are included. Also included are regimens that comprise at least once daily consumption. The skilled artisan will appreciate that the blood level of ketone bodies, or a specific ketone body, achieved may be a valuable measure of dosing frequency. Any frequency, regardless of whether expressly exemplified herein, that allows maintenance of a blood level of the measured compound within acceptable ranges can be considered useful herein. The skilled artisan will appreciate that dosing frequency will be a function of the composition that is being consumed or administered, and some compositions may require more or less frequent administration to maintain a desired blood level of the measured compound (e.g., a ketone body).

As used herein, the term "oral administration" or "orally administering" means that the mammal ingests, or a caretaker is directed to feed, or does feed, the mammal one or more of the compositions described herein. Wherein a human is directed to feed the composition, such direction may be that which instructs and/or informs the human that use of the composition may and/or will provide the referenced benefit, for example, enhancing cognitive function, improving memory, improving liver function, improving learning, improving attention, improving social behavior, improving motor performance, and/or improving cerebrovascular function, or preventing, reducing, or delaying a decline in such foregoing functions or qualities. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition).

The present invention provides a method of treating or preventing diseases of reduced neuronal metabolism, including any age-associated cognitive decline, such as AAMI, and the like, comprising administering an effective amount of a composition comprising at least one compound capable of elevating ketone body concentrations in the body of a mammal (e.g., a patient), e.g., medium chain triglycerides, to a patient in need thereof. Generally, an effective amount is an amount effective to either (1) reduce the symptoms of the disease sought to be treated or (2) induce a change relevant to treating the disease sought to be treated. For any age-associated cognitive decline, such as AAMI, and the like, an effective amount includes an amount effective to: increase cognitive scores; improve memory. As used herein, and discussed elsewhere herein, MCT of this invention are represented by the following formula:

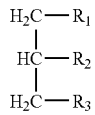

wherein R1, R2, and R3 are independently selected from the group consisting of a fatty acid residue esterified to a glycerol backbone having 5-12 carbons in the carbon backbone ($C_5$ to $C_{12}$ fatty acids), a saturated fatty acid residue esterified to a glycerol backbone having 5-12 carbons in the carbon backbone ($C_5$ to $C_{12}$ fatty acids), an unsaturated fatty acid residue esterified to a glycerol backbone having 5-12 carbons in the carbon backbone ($C_5$ to $C_{12}$ fatty acids), and derivatives of any of the foregoing. The structured lipids of this invention may be prepared by any process known in the art, such as direct esterification, rearrangement, fractionation, transesterification, or the like. For example the lipids may be prepared by the rearrangement of a vegetable oil such as coconut oil.

In one embodiment, the method comprises the use of MCT wherein R1, R2, and R3 are fatty acids containing a six-carbon backbone (tri-C6:0). Tri-C6:0 MCT are absorbed very rapidly by the gastrointestinal tract in a number of animal model systems. The high rate of absorption results in rapid perfusion of the liver, and a potent ketogenic response. In another embodiment, the method comprises the use of MCT wherein R1, R2, and R3 are fatty acids containing an eight-carbon backbone (tri-C8:0). In another embodiment, the method comprises the use of MCT wherein R1, R2, and R3 are fatty acids containing a ten-carbon backbone (tri-C10:0). In another embodiment, the method comprises the use of MCT wherein R1, R2, and R3 are a mixture of C8:0 and C10:0 fatty acids. In another embodiment, the method comprises the use of MCT wherein R1, R2 and R3 are a mixture of C6:0, C8:0, C10:0, and C12:0 fatty acids.

In another embodiment, greater than 95% of R1, R2 and R3 carbon chains of the MCT are 8 carbons in length. In yet another embodiment, the R1, R2, and R3 carbon chains are 6-carbon or 10-carbon chains. In another embodiment, 50% of the R1, R2 and R3 carbon chains of the MCT are 8 carbons in length and about 50% of the R1, R2 and R3 carbon chains of the MCT are about 10 carbons in length. Additionally, utilization of MCT can be increased by emulsification. Emulsification of lipids increases the surface area for action by lipases, resulting in more rapid hydrolysis and release of MCFA. Methods for emulsification of these triglycerides are well known to those skilled in the art.

In one embodiment, the method comprises the use of MCFA of 6, 8, 10 and 12 carbon chain length or mixtures of the above.

In another embodiment, the invention comprises the co-administration of a composition comprising at least one compound capable of elevating ketone body concentrations, such as, for example, emulsified MCT, and L-carnitine or a derivative of L-carnitine. Slight increases in MCFA oxidation have been noted when MCT are combined with L-carnitine (Odle, J., New insights into the utilization of medium-chain triglycerides by the neonate: observations from a piglet model, *J Nutr*, 1997, 127:1061-7). Thus in the present invention emulsified MCT are combined with L-carnitine at doses required to increase the utilization of said MCT. The dosage of L-carnitine and MCT will vary according to the condition of the host, method of delivery, and other factors known to those skilled in the art, and will be of sufficient quantity to raise blood ketone levels to a degree required to treat and prevent AAMI and the like. Derivatives of L-carnitine which may be used in the present invention include but are not limited to decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine.

Therapeutically effective amounts of the therapeutic agents can be any amount or dose sufficient to bring about the desired effect and depend, in part, on the severity and stage of the condition, the size and condition of the patient, as well as other factors readily known to those skilled in the art. The dosages can be given as a single dose, or as several doses, for example, divided over the course of several weeks, as discussed elsewhere herein.

In one embodiment, the ketogenic compounds are administered orally. In another embodiment, the ketogenic compounds are administered intravenously. Oral administration of MCT and other ketogenic compound preparations of intravenous MCT and other ketogenic compound solutions are well known to those skilled in the art.

In one embodiment, oral and/or intravenous administration of a composition comprising at least one compound capable of elevating ketone body concentrations, such as, for example, MCT or MCFA, result in hyperketonemia. Hyperketonemia, in one embodiment, results in ketone bodies being utilized for energy in the brain even in the presence of glucose. Additionally, hyperketonemia results in a substantial (39%) increase in cerebral blood flow (Hasselbalch, S. G., et al., Changes in cerebral blood flow and carbohydrate metabolism during acute hyperketonemia, *Am J Physiol*, 1996, 270: E746-51). Hyperketonemia has been reported to reduce cognitive dysfunction associated with systemic hypoglycemia in normal humans (Veneman, T., et al., Effect of hyperketonemia and hyperlacticacidemia on symptoms, cognitive dysfunction, and counterregulatory hormone responses during hypoglycemia in normal humans, *Diabetes*, 1994, 43:1311-7). Please note that systemic hypoglycemia is distinct from the local defects in glucose metabolism that occur in any age-associated cognitive decline, such as AAMI, and the like.

In all embodiments, the invention provides the subject compositions comprising at least one compound that is capable of elevating ketone body concentrations. Such compounds are also collectively referred to as ketone body precursor compounds or ketogenic compounds. Such compounds include compounds such as, for example, MCT, MCFA, and prodrugs, metabolic precursors, and so on, of ketone bodies. For example, in one embodiment, the compound capable of elevating ketone body concentrations in the body include one or more prodrugs, which can be metabolically converted to the subject compounds by the recipient host. As used herein, a prodrug is a compound that exhibits pharmacological activity after undergoing a chemical transformation in the body. A prodrug can also be referred to as a metabolic precursor if the conversion of the prodrug directly results in the formation of a ketone body. MCT and MCFA must be first oxidized to acetyl-CoA, then undergo several steps before being synthesized into ketone bodies. The class of ketone body precursor compounds include, the compounds described hereinbelow. The ketone body precursor compounds, in one embodiment, are administered in a dosage required to increase blood ketone bodies to a level required to treat and/or prevent the occurrence of any age-associated cognitive decline, such as AAMI, and the like. Appropriate dosages of all of these compounds can be determined by one of skill in the art.

A wide variety of prodrug formulations are known in the art. For example, prodrug bonds may be hydrolyzable, such as esters or anhydrides, or enzymatically biodegradable, such as amides.

Ketone body precursor compounds appropriate for the inventive compositions of the present invention includes any compounds that are capable of directly elevating ketone body concentrations in the body of a mammal, e.g., a patient, and may be determined by one of skill in the art. These compounds can mimic the effect of increasing oxidation of fatty acids and include but are not limited to the ketone bodies, D-μ-hydroxybutyrate and acetoacetate, and metabolic precursors of these. The term metabolic precursor, used in this embodiment, can refer to compounds that comprise 1,3 butane diol, acetoacetyl or D-β-hydroxybutyrate moieties such as acetoacetyl-1-1,3-butane diol, acetoacetyl-D-β-hydroxybutyrate, and acetoacetylglycerol. Esters of any such compound with monohydric, dihydric or trihydric alcohols are also included in yet another embodiment. Metabolic precursors also include polyesters of D-β-hydroxybutyrate, and acetoacetate esters of D-β-hydroxybutyrate. Polyesters of D-β-hydroxybutyrate include oligomers of this polymer designed to be readily digestible and/or metabolized by humans or mammals. These preferably are of 2 to 100 repeats long, typically 2 to 20 repeats long, and most conveniently from 3 to 10 repeats long. Examples of poly D-β-hydroxybutyrate or terminally oxidized poly-D-β-hydroxybutyrate esters useable as ketone body precursors are given below:

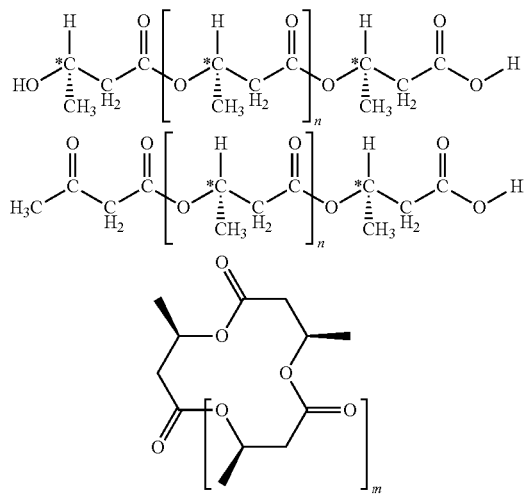

In each case, n is selected such that the polymer or oligomer is readily metabolized on administration to a human or mammal body to provide elevated ketone body levels in blood. Values of n are integers of 0 to 1,000, more preferably 0 to 200, still more preferably 1 to 50, most preferably 1 to 20, particularly conveniently being from 3 to 5. In each case m is an integer of 1 or more, a complex thereof with one or more cations or a salt thereof for use in therapy or nutrition. Examples of cations and typical physiological salts are described herein, and additionally include sodium, potassium, magnesium, calcium, each balanced by a physiological counter-ion forming a salt complex, L-lysine, L-arginine, methyl glucamine, and others known to those skilled in the art.

Also included in the definition of a ketone body precursor compound are several other ketone body precursor compounds useful for treating age associated memory impairment; including esters of polyhydric alcohols, 3-hydroxyacid esters and glycerol esters, as described more fully hereinbelow. As used herein, "derivative" refers to a compound or portion of a compound that is derived from or is theoretically derivable from a parent compound; The term "hydroxyl group" is represented by the formula —OH; the term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below; the term "ester" is represented by the formula —OC(O)R, where R can be an alkyl, alkenyl, alkynyl, aryl, aralkyl, cycloalkyl, halogenated alkyl, or heterocycloalkyl group, as defined below; the term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms; the term "alkenyl group" is defined as a hydrocarbon group of 2 to 24 carbon atoms and structural formula containing at least one carbon-carbon double bond; the term "alkynyl group" is defined as a hydrocarbon group of 2 to 24 carbon atoms and a structural formula containing at least one carbon-carbon triple bond; the term "halogenated alkyl group" is defined as an alkyl group as defined above with one or more hydrogen atoms present on these groups substituted with a halogen (F, Cl, Br, I); the term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous; the term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms; the term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted; the term "aralkyl" is defined as an aryl group having an alkyl group, as defined above, attached to the aryl group. An example of an aralkyl group is a benzyl group; "esterification" refers to the reaction of an alcohol with a carboxylic acid or a carboxylic acid derivative to give an ester; "transesterification" refers to the reaction of an ester with an alcohol to form a new ester compound. The term "3-hydroxybutyrate" is used interchangeably with the term "3-hydroxybutyric acid."

In one embodiment, a compound capable of elevating ketone body concentrations includes compounds according to formula:

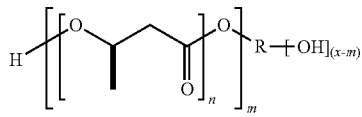

wherein R is a polyhydric alcohol residue; n, m and x represent integers; and m is less than or equal to x.

Physiologically compatible alcohols suitable for forming esters with (R)-3-hydroxybutyrate and derivatives thereof include monohydric and polyhydric alcohols. Esters of polyhydric alcohols deliver a higher density of (R)-3-hydroxybutyrate equivalents per equivalent of (R)-3-hydroxybutyrate derivative using shorter (R)-3-hydroxybutyrate oligomers. Shorter oligomers generally are more readily hydrolyzed to give elevated concentrations of (R)-3-hydroxybutyrate in blood. Examples of polyhydric alcohols suitable for preparing such esters include carbohydrates and carbohydrate derivatives, such as carbohydrate alcohols, examples of carbohydrates include, without limitation, altrose, arabinose, dextrose, erythrose, fructose, galactose, glucose, gulose, idose, lactose, lyxose, mannose, ribose, sucrose, talose, threose, xylose and the like. Additional examples of carbohydrates useful for preparing (R)-3-hydroxybutyrate derivatives include amino derivatives, such as galactosamine, glucosamine and mannosamine, including N-acetyl derivatives, such as N-acetylglucosamine and the like. Examples of carbohydrates also include carbohydrate derivatives, such as alkyl glycosides. Examples of carbohydrate alcohols include, without limitation, glycerol, mannitol, ribitol, sorbitol, threitol, xylitol and the like. The enantiomers of the above-listed carbohydrates and carbohydrate alcohols also can be used to prepare (R)-3-hydroxybutyrate derivatives according to the above formula.

Embodiments include compounds where n is from 1 to about 100; wherein x is from 1 to about 20; wherein m is from 1 to about 20. One embodiment includes a compound wherein R is (R)-1,3-butanediol.

In another embodiment, compounds capable of elevating ketone body concentrations include compounds of the formula

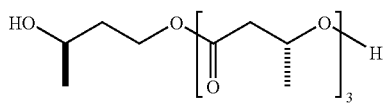

and also

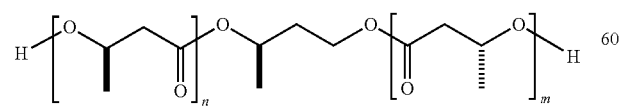

where n and m independently are integers from 1 to about 100. In some embodiments, n and m are the same; n and m are different; and wherein n and m are 3. In addition, compounds capable of elevating ketone body concentrations include ester compounds of R-3-hydroxybutyrate according to the formula

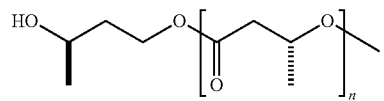

wherein n is an integer from 1 to about 100. In one embodiment, n is 3.

Other compounds capable of elevating ketone body levels include 3-hydroxyacids. The compositions include 3-hydroxyacids, linear or cyclic oligomers thereof, esters of the 3-hydroxyacids or oligomers, derivatives of 3-hydroxyacids, and combinations thereof. In one embodiment, the compositions include the cyclic macrolide of R-3-hydroxyacids containing 3, 4, or 5 monomeric subunits. 3-hydroxyacids include 3-hydroxybutyric acid, 3-hydroxyvaleric acid, 3-hydroxyhexanoic acid and 3-hydroxyheptanoic acid. In some embodiments, the length of the oligomer must be such that the derivative has a suitable digestion rate for sustained release of monomer. In another embodiment, the cyclic trimer (triolide) is used in a combination with other cyclic oligolides or linear esters and/or mixtures of both.

The general formula for 3-hydroxyacids is:

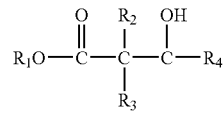

$R_1$ is selected from hydrogen, methyl, alkyl, alkenyl, aryl, arylalkyl, heteroalkyl, heteroaryl, thiol, disulfide, ether, thiol ether, amine, amide, halogen. $R_2$ and $R_3$ are independently selected from hydrogen, methyl, alkyl, alkenyl, aryl, arylalkyl, heteroalkyl, heteroaryl, thiol, disulfide, ether, thiol ether, amine, amide, halogen, hydroxy, ester, nitrogen-substituted radicals, and/or oxygen-substituted radicals. $R_4$ is selected from hydrogen, alkyl, alkenyl, aryl, arylalkyl, heteroalkyl, heteroaryl, thiol, disulfide, ether, thiol ether, amine, amide, halogen, hydroxy, ester, nitrogen-substituted radicals, and/or oxygen-substituted radicals. Further, when $R_4$ is not hydrogen or a halogen, $R_3$ can be a direct bond to and $R_4$ can be methyl.

Other compounds capable of elevating ketone body levels include glycerol esters, namely, not readily water-soluble glycerides of at least one keto or hydroxy acid, having the formula

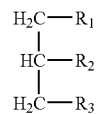

wherein two or three of the groups $R_1$, $R_2$ and $R_3$ independently of each other, are one or more of the groups acetoacetate, alpha-ketopropionate, beta-hydroxybutyrate and alpha-hydroxypropionate, and when only two of the groups $R_1$, $R_2$ and $R_3$ are any of said groups, the third of them is a hydroxy group or a residue of a saturated or unsaturated fatty acid containing 2 to 24 carbon atoms. Other glycerol esters are envisioned, particularly not readily water-soluble glycerides of at least one keto or hydroxy acid, having the formula

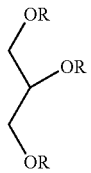

wherein one R group is hydrogen, and two R groups are (—COCH$_2$, COCH$_3$). Additionally, wherein each R is the same or different and is hydrogen, or (—COCH$_2$, COCH$_3$), provided that at least one R is not hydrogen and wherein R' is a linear acid ester of even carbon number from 2 to 20 carbons.

This invention also provides the inventive compositions in one embodiment in administratively convenient formulations including dosage units incorporated into a variety of containers. Dosages of the inventive compositions, such as, for example, those comprising MCT, may be administered in an effective in an effective amount to increase the cognitive ability of patients afflicted with diseases of reduced neuronal metabolism, such as in patients with any age-associated cognitive decline, such as, AAMI, and the like.

In one embodiment, the inventive compositions result in elevating ketone concentrations in the body, and in this embodiment, the compositions are administered in an amount that is effective to induce hyperketonemia. In one embodiment, hyperketonemia results in ketone bodies being utilized for energy in the brain.

In one embodiment, the composition increases the circulating concentration of at least one type of ketone body in the mammal or patient. In one embodiment, the circulating ketone body is D-beta-hydroxybutyrate. The amount of circulating ketone body can be measured at a number of times post administration, and in one embodiment, is measured at a time predicted to be near the peak concentration in the blood, but can also be measured before or after the predicted peak blood concentration level. Measured amounts at these off-peak times are then optionally adjusted to reflect the predicted level at the predicted peak time. In one embodiment, the predicted peak time is at about two hours. Peak circulating blood level and timing can vary depending on factors known to those of skill in the art, including individual digestive rates, co-ingestion or pre- or post-ingestion of foods, drinks, etc., as known to one of skill in the art. In one embodiment, the peak blood level reached of D-beta-hydroxybutyrate is between about 0.05 millimolar (mM) to about 50 mM. Another way to determine whether blood levels of D-beta-hydroxybutyrate are raised to about 0.05 to about 50 mM is by measurement of D-beta-hydroxybutyrate urinary excretion a range in the range of about 5 mg/dL to about 160 mg/dL. In other embodiments, the peak blood level is raised to about 0.1 to about 40 mM, from about 0.1 to about 20 mM, from about 0.1 to about 10 mM, to about 0.1 to about 5 mM, more preferably raised to about 0.15 to about 2 mM, from about 0.15 to about 0.3 mM, although variations will necessarily occur depending on the formulation and host, for example, as discussed above. In other embodiments, the peak blood level reached of D-beta-hydroxybutyrate will be at least about 0.05 mM, at least about 0.1 mM, at least about 0.15 mM, at least about 0.2 mM, at least about 0.5 mM, at least about 1 mM, at least about 1.5 mM, at least about 2 mM, at least about 2.5 mM, at least about 3 mM, at least about 4 mM, at least about 5 mM, at least about 10 mM, at least about 15 mM, at least about 20 mM, at least about 30 mM, at least about 40 mM, and at least about 50 mM.

Effective amount of dosages of compounds for the inventive compositions, i.e., compounds capable of elevating ketone body concentrations in an amount effective for the treatment of or prevention of loss of cognitive function caused by reduced neuronal function in AAMI will be apparent to those skilled in the art. As discussed herein above, such effective amounts can be determined in light of disclosed blood ketone levels. Where the compound capable of elevating ketone body concentrations is MCT, the MCT dose, in one embodiment, is in the range of about 0.05 g/kg/day to about 10 g/kg/day of MCT. In other embodiments, the dose will be in the range of about 0.25 g/kg/day to about 5 g/kg/day of MCT. In other embodiments, the dose will be in the range of about 0.5 g/kg/day to about 2 g/kg/day of MCT. In other embodiments, the dose will be in the range of about 0.1 g/kg/day to about 2 g/kg/day. In other embodiments, the dose of MCT is at least about 0.05 g/kg/day, at least about 0.1 g/kg/day, at least about 0.15 g/kg/day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, and at least about 50 g/kg/day.

Convenient unit dosage containers and/or formulations include tablets, capsules, lozenges, troches, hard candies, nutritional bars, nutritional drinks, metered sprays, creams, and suppositories, among others. The compositions may be combined with a pharmaceutically acceptable excipient such as gelatin, oil(s), and/or other pharmaceutically active agent(s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with antioxidants, compounds that enhance the efficiency of glucose utilization, and mixtures thereof.

In one embodiment, the subject is intravenously infused with ketogenic compounds such as MCT, MCFA, directly, to a level required to treat and prevent the occurrence of diseases of reduced neuronal metabolism, in patients with any age-associated cognitive decline, such as AAMI, and the like. Preparation of intravenous lipids and ketone body solutions are well known to those skilled in the art.

In one embodiment, the invention provides a formulation comprising a mixture of MCT and carnitine to provide elevated blood ketone levels. The nature of such formulations will depend on the duration and route of administration. Such formulations can be in the range of 0.05 g/kg/day to 10 g/kg/day of MCT and 0.05 mg/kg/day to 10 mg/kg/day of carnitine or its derivatives. In one embodiment, an MCT dose can be in the range of 0.05 g/kg/day to 10 g/kg/day of MCT. The dose can be in the range of 0.25 g/kg/day to 5 g/kg/day of MCT. The dose can also be in the range of 0.5 g/kg/day to 2 g/kg/day of MCT. In some embodiments, a carnitine or carnitine derivative dose can be in the range of 0.05 mg/kg/day to 10 mg/kg/day. The carnitine or carnitine derivative dose can be in the range of 0.1 mg/kg/day to 5 mg/kg/day. The carnitine or carnitine derivative dose can also be in the range of 0.5 mg/kg/day to 1 mg/kg/day. Variations will necessarily occur depending on the formulation and/or host, for example.

In one embodiment, a formulation comprises a range of about 1 to about 500 g of emulsified MCT combined with about 1 to about 2000 mg of carnitine. Amounts of MCT can be at least about 1 g, at least about 10 g, at least about 50 g, at least about 100 g, at least about 150 g, at least about 200 g, at least about 250 g, at least about 300 g, at least about 400 g. Amounts of carnitine can be at least about 1 g, at least about 50 g, at least about 100 g, at least about 250 g, at least about 500 g, at least about 1000 g, at least about 1250 g, at least about 1500 g. Another formulation comprises 50 g MCT (95% triC8:0) emulsified with 50 g of mono- and di-glycerides combined with 500 mg of L-carnitine. Such a formulation is well tolerated and generally induces hyperketonemia for 3-4 hours in healthy human subjects.

The daily dose of MCT can be also be measured in terms of grams of MCT per kg of body weight (BW) of the mammal. The daily dose of MCT can range from about 0.01 g/kg to about 10.0 g/kg BW of the mammal. Preferably, the daily dose of MCT is from about 0.1 g/kg to about 5 g/kg BW of the mammal. More preferably, the daily dose of MCT is from about 0.2 g/kg to about 3 g/kg of the mammal. Still more preferably, the daily dose of MCT is from about 0.5 g/kg to about 2 g/kg of the mammal.

In some embodiments, the inventive compounds may be co administered with carbohydrate, or be co-formulated with carbohydrate. Carbohydrate can include more than one type of carbohydrate. Appropriate carbohydrates are known in the art, and include simple sugars, such as glucose, fructose, sucrose, and the like. If co-formulated, the amount of carbohydrate to use can include at least about 0.1 g, at least about 1 g, at least about 10 g, at least about 50 g, at least about 100 g, at least about 150 g, at least about 200 g, at least about 250 g, at least about 300 g, at least about 400 g. Amounts of carnitine can be at least about 1 g, at least about 50 g, at least about 100 g.

In another embodiment, the methods of the present invention further comprise determination of the patients' genotype or particular alleles. In one embodiment, the patient's alleles of the apolipoprotein E gene are determined. In some examples, the inventor teaches that non-E4 carriers performed better than those with the E4 allele when elevated ketone body levels were induced with MCT. Also, those with the E4 allele had higher fasting ketone body levels and the levels continued to rise at the two hour time interval. Therefore, E4 carriers may require higher ketone levels or agents that increase the ability to use the ketone bodies that are present. Accordingly, an embodiment consists of a dose of MCT combined with agents that increase the utilization of fats, MCT or ketone bodies. Examples of agents that increase utilization of fatty acids may be selected from a group comprising of, but not limited to, non-steroidal anti-inflammatory agents (NSAIDs), statin drugs (such as Lipitor® and Zocor®) and fibrates. Examples of NSAIDs include: aspirin, ibuprofen (Advil, Nuprin, and others), ketoprofen (Orudis KT, Actron), and naproxen (Aleve).

NSAIDs function, in part, as PPAR-gamma agonists. Increasing PPAR-gamma activity increases the expression of genes associated with fatty acid metabolism such as FATP (for review, see (Gelman, L., et al., An update on the mechanisms of action of the peroxisome proliferator-activated receptors (PPARs) and their roles in inflammation and cancer, *Cell Mol Life Sci*, 1999, 55:932-43)). Accordingly, a combination of MCT and PPAR-gamma agonists will prove beneficial to patients with decreased neuronal metabolism. In one embodiment the PPAR-gamma agonist is an NSAID.

Statins are a class of drugs with pleiotropic effects, the best characterized being inhibition of the enzyme 3-hydroxy-3-methylglutaryl CoA reductase, a key rate step in cholesterol synthesis. Statins also have other physiologic affects such as vasodilatory, anti-thrombotic, antioxidant, anti-proliferative, anti-inflammatory and plaque stabilizing properties. Additionally, statins cause a reduction in circulating triglyceride rich lipoproteins by increasing the levels of lipoprotein lipase while also decreasing apolipoprotein CIII (an inhibitor of lipoprotein lipase) (Schoonjans, K., et al., 3-Hydroxy-3-methylglutaryl CoA reductase inhibitors reduce serum triglyceride levels through modulation of apolipoprotein C-III and lipoprotein lipase, *FEBS Lett*, 1999, 452:160-4). Accordingly, administration of statins results in increased fatty acid usage, which can act synergistically with MCT administration. This should prove especially beneficial to ApoE4 carriers. One embodiment of this invention would be combination therapy consisting of statins and MCT.

Fibrates, such as Bezafibrate, ciprofibrate, fenofibrate and Gemfibrozil, are a class of lipid lowering drugs. They act as PPAR-alpha agonists and similar to statins they increase lipoprotein lipase, apoAI and apoAII transcription and reduce levels of apoCIII (Staels, B., et al., Mechanism of action of fibrates on lipid and lipoprotein metabolism, *Circulation*, 1998, 98:2088-93). As such they have a major impact on levels of triglyceride rich lipoproteins in the plasma, presumably by increasing the use of fatty acids by peripheral tissues. Accordingly, the present invention discloses that fibrates alone or in combination with MCT would prove beneficial to patients with reduced neuronal metabolism such as those with any age-associated cognitive decline, such as AAMI and the like.

Caffeine and ephedra alkaloids are commonly used in over the counter dietary supplements. Ephedra alkaloids are commonly derived from plant sources such as ma-huang (*Ephedra sinica*). The combination of caffeine and ephedra stimulate the use of fat. Ephedra alkaloids are similar in structure to adrenaline and activate beta-adenergic receptors on cell surfaces. These adenergic receptors signal through cyclic AMP (cAMP) to increase the use of fatty acids. cAMP is normally degraded by phosphodiesterase activity. One of the functions of caffeine is to inhibit phosphodiesterase activity and thereby increase cAMP mediated signaling. Therefore caffeine potentiates the activity of the ephedra alkaloids. Accordingly, the present invention discloses that ephedra alkaloids alone can provide a treatment or prevention for conditions of reduced neuronal metabolism. Additionally, it is disclosed that ephedra alkaloids in combination with caffeine can provide a treatment or prevention for conditions of reduced neuronal metabolism. Accordingly, it is disclosed that a combination of MCT with ephedra, or MCT with caffeine, or MCT, ephedra alkaloids and caffeine together can provide a treatment or prevention for diseases of reduced neuronal metabolism, in patients with any age-associated cognitive decline, such as AAMI, and the like.

Ketone bodies are used by neurons as a source of Acetyl-CoA. Acetyl-CoA is combined with oxaloacetate to form citrate in the Krebs' cycle, or citric acid cycle (TCA cycle). It is important for neurons to have a source of Acetyl-CoA as well as TCA cycle intermediates to maintain efficient energy metabolism. Yet, neurons lose TCA cycle intermediates to synthesis reactions, such as the formation of glutamate. Neurons also lack pyruvate carboxylase and malic enzyme so they cannot replenish TCA cycle intermediates from pyruvate (Hertz, L., et al., Neuronal-astrocytic and cytosolic-mitochondrial metabolite trafficking during brain activation, hyperammonemia and energy deprivation, *Neurochem Int*, 2000, 37:83-102). Accordingly, the present invention discloses that a combination of ketone bodies with a source of TCA cycle intermediates, in one embodiment. TCA cycle intermediates are selected from a group consisting of citric acid, aconitic acid, isocitric acid, α-ketoglutaric acid, succinic acid, fumaric acid, malic acid, oxaloacetic acid, and mixtures thereof. One embodiment of the invention is a combination of TCA cycle intermediates with MCT in a formulation to increase efficiency of the TCA.

Another source of TCA cycle intermediates are compounds that are converted to TCA cycle intermediates within the body (TCA intermediate precursors). Examples of such compounds are 2-keto-4-hydroxypropanol, 2,4-dihydroxybutanol, 2-keto-4-hydroxybutanol, 2,4-dihydroxybutyric acid, 2-keto-4-hydroxybutyric acid, aspartates as well as mono- and di-alkyl oxaloacetates, pyruvate and glucose-6-phosphate. Accordingly, the present invention discloses that a combination of TCA intermediate precursors with ketone bodies will be beneficial for the treatment and prevention of diseases resulting from reduced metabolism. Also, the present invention discloses that MCT combined with TCA intermediate precursors will be beneficial for the treatment and prevention of diseases resulting from reduced metabolism.

The present invention further discloses that additional sources of TCA cycle intermediates and Acetyl-CoA can be advantageously combined with ketone body therapy. Sources of TCA cycle intermediates and Acetyl-CoA include mono- and di-saccharides as well as triglycerides of various chain lengths and structures.

Further benefit can be derived from formulation of a pharmaceutical composition that includes metabolic adjuvants. Metabolic adjuvants include vitamins, minerals, antioxidants and other related compounds. Such compounds may be chosen from a list that includes but is not limited to; ascorbic acid, biotin, calcitriol, cobalamin, folic acid, niacin, pantothenic acid, pyridoxine, retinol, retinal (retinaldehyde), retinoic acid, riboflavin, thiamin, a-tocopherol, phytylmenaquinone, multiprenylmenaquinone, calcium, magnesium, sodium, aluminum, zinc, potassium, chromium, vanadium, selenium, phosphorous, manganese, iron, fluorine, copper, cobalt, molybdenum, iodine. Accordingly a combination of ingredients chosen from: metabolic adjuvants, compounds that increase ketone body levels, and TCA cycle intermediates, will prove beneficial for treatment and prevention of diseases of reduced neuronal metabolism, in patients with any age-associated cognitive decline, such as AAMI, and the like.

Administration of compositions comprising at least one compound capable of elevating ketone body concentrations, such as MCT, including triglycerides composed of C6 and C8 fatty acid residues, can result in elevated ketone body levels even if large amounts of carbohydrate are consumed at the same time (for overview see (Odle, J., New insights into the utilization of medium-chain triglycerides by the neonate: observations from a piglet model, *J Nutr,* 1997, 127:1061-7); see also copending U.S. Patent Provisional Patent Application Ser. No. 60/323,995, "Drug Targets for Alzheimer's Disease and Other Diseases Associated with Decreased Neuronal Metabolism," filed Sep. 21, 2001). The advantages of the Applicant's approach are clear, since careful monitoring of what is eaten is not required and compliance is much simpler.

Further benefit can be derived from formulation of a pharmaceutical composition comprising a composition comprising at least one compound capable of elevating ketone body concentrations in the mammal with other therapeutic agents in patients with any age-associated cognitive decline, such as AAMI, and the like. Such therapeutic agents include acetylcholinesterase inhibitors, acetylcholine synthesis modulators, acetylcholine storage modulators, acetylcholine release modulators, anti-inflammatory agents, estrogen or estrogen derivatives, insulin sensitizing agents, β-amyloid plaque removal agents (including vaccines), inhibitors of β-amyloid plaque formation, γ-secretase modulators, pyruvate dehydrogenase complex modulators, neurotrophic growth factors (e.g., BDNF), ceramides or ceramide analogs, and/or NMDA glutamate receptor antagonists (for overview of such treatments, see (Selkoe, D. J., Alzheimer's disease: genes, proteins, and therapy, *Physiol Rev,* 2001, 81:741-66) (Bullock, R., New drugs for Alzheimer's disease and other dementias, *Br J Psychiatry,* 2002, 180:135-9)). While such treatments are still in the experimental stage it is the novel insight of the present invention that said treatments be advantageously combined with increased fatty acid/ketone body usage as described herein.

From the description above, a number of advantages of the invention for treating and preventing diseases of reduced neuronal metabolism, in patients with any age-associated cognitive decline, such as AAMI, and the like, become evident:

(a) Current treatments for diseases of reduced neuronal metabolism, in patients with any age-associated cognitive decline, such as AAMI, and the like, are merely palliative and do not address the reduced neuronal metabolism associated with these conditions. Ingestion of the inventive compositions as a nutritional supplement is a simple method to provide neuronal cells, in which glucose metabolism is compromised, with ketone bodies as a metabolic substrate.

(b) Increased blood levels of ketone bodies can be achieved by a composition or regimen rich in ketogenic compositions such as medium chain triglycerides.

(c) Many ketogenic compounds, such as medium chain triglycerides, can be infused intravenously into patients or administered orally.

(d) Levels of ketone bodies can be easily measured in urine or blood by commercially available products (e.g., Ketostix®, Bayer, Inc.).

According to the invention, disclosed is use of ketogenic compounds, such as MCT or MCFA, as a treatment and preventative measure of diseases of reduced neuronal metabolism, in patients with any age-associated cognitive decline, such as AAMI, and the like, which provides a novel means of alleviating reduced neuronal metabolism associated with these conditions. It is the novel and significant insight of the present invention that use of ketogenic compounds such as MCT and MCFA results in hyperketonemia which will provide increased neuronal metabolism for diseases of reduced neuronal metabolism in patients with any age-associated cognitive decline, such as AAMI, and the like. Although the description above contains much specificity, these should not be construed as limiting the scope of the invention but merely as providing illustrations for some of the embodiments of this invention. For example, supplementation with ketogenic compounds such as MCT may prove more effective when combined with insulin sensitizing agents such as vanadyl sulfate, chromium picolinate, and vitamin E. Such agents may function to increase glucose utilization in compromised neurons and work synergistically with hyperketonemia. In another example ketogenic compounds such as MCT can be combined with compounds that increase the rates of fatty acid utilization such as L-carnitine and its derivatives. Mixtures of such compounds may synergistically increase levels of circulating ketone bodies.

In some embodiments, the mammal is specifically a human. Other mammals within the scope of this invention are mammals such as companion animals, such as a pet or mammal in the care of a human for whether for a long term or briefly. In some embodiments, the companion mammal is a dog or cat.

In one embodiment, the mammal is a healthy aging mammal, as defined herein above. In such embodiments, the mammal will not be known to have overt signs or substantial symptoms or indicia of cognitive impairment, as determined by a skilled artisan. Although the mammal may have other health issues, even age-related health issues, they will be of such character as to not substantially impact the cognitive, motor, or behavioral functioning of the mammal. Thus, the skilled artisan will appreciate that it may be impossible to classify an aging or geriatric mammal as completely "healthy"—it is not necessary to do so to practice the methods and compositions provided herein. In other embodiments, the aging mammal is specifically understood to have age-related cognitive impairment, whether determined by formal diagnosis, or by its evidencing hallmarks of cognitive, memory, or motor impairments or behavioral indicia of such impairment or the like. In one embodiment, the mammal has a characteristic or phenotype associated with age-related cognitive impairment, for example the mammal has one or more of the following characteristic or phenotypic expressions of cognitive, motor, or behavioral difficulties associated with age. For example, decreased ability to recall, short-term memory loss, decreased learning rate, decreased capacity for learning, decreased problem solving skills, decreased attention span, decreased motor performance, increased confusion, or dementia, as compared to a control mammal not having the phenotype.

In one embodiment, the compositions of the invention are food compositions, such as pet foods. In certain embodiments, the composition is a food composition, further comprising in addition to the MCT, about 15-50% protein, 5-40% fat, 5-40% carbohydrate, each on a dry weight basis, and having a moisture content of 5-20%. In certain embodiments, the foods are intended to supply complete necessary dietary requirements. Also provided are compositions that are useful as snacks, nutrition bars, or other forms of food products or nutritional or dietary supplements, including tablets, capsules, gels, pastes, emulsions, caplets, and the like as discussed below. Optionally, the food compositions can be a dry composition, semi-moist composition, wet composition, or any mixture thereof.

In another embodiment, the compositions of the invention are food products formulated specifically for human consumption. These will include foods and nutrients intended to supply necessary dietary requirements of a human being as well as other human dietary supplements. In a one embodiment, the food products formulated for human consumption are complete and nutritionally balanced, while in others they are intended as nutritional supplements to be used in connection with a well-balanced or formulated diet.

In another embodiment, the composition is a food supplement, such as drinking water, beverage, liquid concentrate, gel, yoghurt, powder, granule, paste, suspension, chew, morsel, treat, snack, pellet, pill, capsule, tablet, or any other delivery form. The nutritional supplements can be specially formulated for consumption by a particular species or even an individual mammal, such as companion mammal, or a human. In one embodiment, the nutritional supplement can comprise a relatively concentrated dose of MCT such that the supplement can be administered to the mammal in small amounts, or can be diluted before administration to a mammal. In some embodiments, the nutritional supplement or other MCT-containing composition may require admixing with water or the like prior to administration to the mammal, for example to adjust the dose, to make it more palatable, or to allow for more frequent administration in smaller doses.

The MCT-containing compositions may be refrigerated or frozen. The MCT may be pre-blended with the other components of the composition to provide the beneficial amounts needed, may be emulsified, coated onto a pet food composition, nutritional or dietary supplement, or food product formulated for human consumption, or may be added to a composition prior to consuming it or offering it to a mammal, for example, using a powder or a mix.

In one embodiment, the compositions comprise MCT in an amount effective to enhance cognitive function and behavior in a mammal to which the composition has been administered. For formulations formulated for human consumption, the amount of MCT as a percentage of the composition is in the range of about 1% to about 50% of the composition on a dry matter basis, although a lesser or greater percentage can be supplied. In various embodiments, the amount is about 1.0%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%. 30%, 31%, 32%, 33%, 34%, 35%, 36%, 37%, 38%, 39%, 40%, 41%, 42%, 43%, 44%, 45%, 46%, 47%, 48%, 49%, 50% or more, of the composition on a dry weight basis. Nutritional supplements may be formulated to contain several fold higher concentrations of MCT, to be amenable for administration to a mammal in the form of a tablet, capsule, liquid concentrated, or other similar dosage form, or to be diluted before administrations, such as by dilution in water, spraying or sprinkling onto a pet food, and other similar modes of administration. For a nutritional or dietary supplement, MCT alone may be administered directly to the mammal or applied directly to the mammal's regular food. Nutritional or dietary supplement formulations in various embodiments contain about 30% to about 100% MCT, although lesser amounts may also used.

Sources of the MCT include any suitable source, semi-synthetic, synthetic or natural. Examples of natural sources of MCT include plant sources such as coconuts and coconut oil, palm kernels and palm kernel oils, and animal sources such as milk from any of a variety of species, e.g., goats.

In various embodiments, the compositions optionally comprise supplementary substances such as minerals, vitamins, salts, condiments, colorants, and preservatives. Non-limiting examples of supplementary minerals include calcium, phosphorous, potassium, sodium, iron, chloride, boron, copper, zinc, magnesium, manganese, iodine, selenium, and the like. Non-limiting examples of supplementary vitamins include vitamin A, any of the B vitamins, vitamin C, vitamin D, vitamin E, and vitamin K, including various salts, esters, or other derivatives of the foregoing. Additional dietary supplements may also be included, for example, any form of niacin, pantothenic acid, inulin, folic acid, biotin, amino acids, and the like, as well as salts and derivatives thereof. In addition, the compositions may comprise beneficial long chain polyunsaturated fatty acids such as the (n-3) and/or (n-6) fatty acids, arachidonic acid, eicosapentaenoic acid, docosapentaenoic acid, and docosahexaenoic acid, as well combinations thereof.

The compositions provided herein optionally comprise one or more supplementary substances that promote or sustain general neurologic health, or further enhance cognitive function. Such substances include, for example, choline, phosphatidylserine, alpha-lipoic acid, CoQ10, acetyl-L-carnitine, and herbal extracts such as *Gingko biloba*, *Bacopa monniera*, *Convolvulus pluricaulis*, and *Leucojum aestivum*.

In various embodiments, the pet food or dietary supplement compositions provided herein preferably comprise, on a dry weight basis, from about 15% to about 50% crude protein. The crude protein material comprise one or more proteins from any source whether animal, plant, or other. For example, vegetable proteins such as soybean, cottonseed, and peanut are suitable for use herein. Animal proteins such as casein, albumin, and meat protein, including pork, lamb, equine, poultry, fish, or mixtures thereof are useful.

The compositions may further comprise, on a dry weight basis, from about 5% to about 40% fat. The compositions may further comprise a source of carbohydrate. The compositions typically comprise from about 15% to about 40% carbohydrate, on a dry weight basis. Examples of such carbohydrates include grains or cereals such as rice, corn, sorghum, alfalfa, barley, soybeans, canola, oats, wheat, or mixtures thereof. The compositions also optionally comprise other components that comprise carbohydrates such as dried whey and other dairy products or by-products.

In certain embodiments, the compositions also comprise at least one fiber source. Any of a variety of soluble or insoluble fibers suitable for use in foods or feeds may be utilized, and such will be known to those of ordinary skill in the art. Presently included fiber sources include beet pulp (from sugar beet), gum arabic, gum talha, psyllium, rice bran, carob bean gum, citrus pulp, pectin, fructooligosaccharide additional to the short chain oligofructose, mannanoligofructose, soy fiber, arabinogalactan, galactooligosaccharide, arabinoxylan, or mixtures thereof. Alternatively, the fiber source can be a fermentable fiber. Fermentable fiber has previously been described to provide a benefit to the immune system of a companion animal. Fermentable fiber or other compositions known to those of skill in the art which provide a prebiotic composition to enhance the growth of probiotic microorganisms within the intestine may also be incorporated into the composition to aid in the enhancement of the benefit provided by the present invention to the immune system of an mammal. Additionally, probiotic microorganisms, such as *Lactobacillus* or *Bifidobacterium* species, for example, may be added to the composition. The skilled artisan will understand how to determine the appropriate amount of MCT to be added to a given composition. Such factors that may be taken into account include the type of composition (e.g., food composition, drink, dietary supplement, or food product formulated for human consumption), the average consumption of specific types of compositions by different mammals, the intended or required dose of MCT, the palatability and acceptability of the final product for the intended recipient or consumer, the manufacturing conditions under which the composition is prepared, the convenience for the purchaser, and packaging considerations. Preferably, the concentrations of MCT to be added to the composition are calculated on the basis of the energy and nutrient requirements of the mammal. The MCT can be added at any time during the manufacture and/or processing of the composition whether as part of a formulation of a pet food composition, dietary supplement, or food product for human consumption, or as a coating or additive to any of the foregoing.

The present invention also relates to a method for treatment of age related cognitive decline or AAMI, comprising the steps of identifying a population of healthy aging mammals having AAMI, dividing the population into at least a control group and one or more test groups, formulating at least one delivery system for delivering a composition comprising at least one compound capable of elevating ketone body concentrations in an amount effective for elevating at least one type of ketone body in the blood of an individual mammal, wherein, on an extended regular basis, each test group receives a formulation delivering a composition comprising at least one compound capable of elevating ketone body concentrations in an amount effective for elevating at least one type of ketone body in the blood of an individual mammal and the control group does not receive any composition comprising at least one compound capable of elevating ketone body concentrations in an amount effective for elevating at least one type of ketone body in the blood of an individual mammal. The method further comprises comparing at least one neuropsychological test result in the control and test groups, determining which of the delivery systems for delivering the composition comprising at least one compound capable of elevating ketone body concentrations in an amount effective for elevating at least one type of ketone body in the blood of an individual mammal was effective in improving the results of at least one neuropsychological test; and administering a treatment-based delivery system determined in the previous step to a population of aging mammals, thereby treating AAMI.

EXAMPLES

The following examples are provided for illustrative purposes only and are not intended to limit the scope of the invention.

Example 1

Nutritional Drink

Nutritional drinks are prepared comprising the following ingredients: emulsified MCT in the range of 5 to 100 g/drink, L-carnitine in the range of 0.1 to 1 gram/drink, mix of vitamins and minerals at recommended daily levels, and a variety of flavorings.

Example 2

Additional Formulations

Additional formulations can be in the form of Ready to Drink Beverages, Powdered Beverages, Nutritional Drinks, Food Bars, Puddings, other confections and the like. Formulations for such are clear to those skilled in the art.

A. Ready to Drink Beverage Ready to Drink Beverages are prepared so as to comprise the following ingredients: emulsified MCT in the range of 5-100 g/drink, L-carnitine in the range of 100-1000 mg/drink, and a variety of flavorings and other ingredients used to increased palatability, stability, etc.

B. Powdered Beverages MCT may be prepared in a dried form, useful for food bars and powdered beverage preparations. A powdered beverage may be prepared so as to comprise the following components per drink: dried emulsified MCT in the range of 10-50 g, L-carnitine in the range of 250-500 mg, sucrose in the range of 8-15 g, maltodextrin in the range of 1-5 g, flavorings 0-1 g and other ingredients used to increased palatability, stability, etc.

C. Food Bar A food bar would be comprised of: dried emulsified MCT 0.1-50 g, L-carnitine 250-500 mg, glycerin 1-5 g, corn syrup solids 5-25 g, cocoa 2-7 g, coating 15-25 g.

D. Gelatin Capsules Hard or soft gelatin capsules are prepared using the following ingredients: MCT 0.1-1000 mg/capsule, L-carnitine 250-500 mg/capsule, Starch, NF 0-600 mg/capsule; Starch flowable powder 0-600 mg/capsule; Silicone fluid 350 centistokes 0-20 mg/capsule. The ingredients are mixed, passed through a sieve, and filled into capsules.

E. Tablets Tablets are prepared so as to comprise the following ingredients: MCT 0.1-1000 mg/tablet; L-carnitine 250-500 mg/tablet; Microcrystalline cellulose 20-300 mg/tablet; Starch 0-50 mg/tablet; Magnesium stearate or stearate acid 0-15 mg/tablet; Silicon dioxide, fumed 0-400 mg/tablet; silicon dioxide, colloidal 0-1 mg/tablet, and lactose 0-100 mg/tablet. The ingredients are blended and compressed to form tablets.

F. Suspensions Suspensions are prepared so as to comprise the following ingredients: 0.1-1000 mg MCT; 250-500 mg L-carnitine; Sodium carboxymethyl cellulose 50-700 mg/5 ml; Sodium benzoate 0-10 mg/5 ml; Purified water 5 ml; and flavor and color agents as needed.

G. Parenteral Solutions A parenteral composition is prepared by stirring so as to comprise 1.5% by weight of MCT and L-carnitine in 10% by volume propylene glycol and water. The solution is made isotonic with sodium chloride and sterilized.

Example 3

Improvement in Cognitive Function in an Elderly Population with Treatment with Medium Chain Triglycerides The study recruited four elderly subjects, two males and two females. Average age was 54.24 years. All subjects were free from any significant medical, neurological, or psychiatric illness. Subjects were taking no central nervous system medications. Subjects were asked to fast overnight for approximately 12 hours on the night prior to the study visit. They arrived in the morning and baseline measurements were taken on three tests: a measure of simple reaction time, a memory scanning paradigm and a mental rotation task. Each test included a set of practice measurements which were not recorded. The practice tests are designed to minimize practice effects of repeated testing. The subjects then consumed the test article, waited 1 hour and then all three tests were repeated.

Test article. The test article comprised 20 grams of a 50% medium chain triglyceride/50% corn starch powder mixed with Ensure™. The test article delivered a total of 10 grams of medium chain triglycerides. The subjects were asked to consume the test article in 10 minutes or less.

Reaction time. The reaction time test measured reaction to a stimulus presented on a computer screen. The subject's task was to press the Z key if the stimulus appeared on the left portion of the screen and the/key if the stimulus appeared on the right side of the screen. Reaction time was measured in milliseconds. If the response was incorrect or greater than 1500 milliseconds then the default value of 1500 ms was assigned. Each session comprised 9 blocks of 50 measurements. The first 3 blocks were practice blocks that were not recorded and meant to minimize practice effects in the test. Therefore, 6 blocks of 50 measurements each were recorded per session for a total of 300 individual measurements.

Memory Scanning. The memory scanning task measured the ability of the subject to briefly hold a set of numbers in short term memory. The subject is presented with a set of digits "to be remembered". The number of digits varied between 1 to 6 digits. After a brief delay of 500 ms the subject was then presented with a "probe" digit. The subject's task was to remember if the probe digit was present in the "to be remembered" set of digits. If the probe digit was included in the "to be remembered" set, then subject pressed the/key on the keyboard. If the probe digit was not in the "to be remembered set", the subject pressed the Z key. Both correct answers and the time it takes to respond were recorded. Each session comprised of 6 blocks of 48 trials. The first block was a practice block was not recorded and meant to minimize practice effects in the test. Therefore, 5 blocks of 48 measurements were recorded per session for a total of 240 individual measurements.

Mental Rotation. The mental rotation task measured how quickly the subjects could mentally rotate an object. On each trial, the subject was presented with a symbol resembling an upper-case 'F'. The symbol was presented at one of eight orientations, and was either a letter 'F' or the mirror-image of an 'F'. The subject's task was to determine whether the symbol was a normal or a reversed 'F', and to respond as quickly as possible by pushing the Z key if the symbol was reversed, or the/key if the symbol was not reversed. If the response was incorrect, or if an invalid key was pressed, a brief tone was heard and the maximum time (1500 ms) was assigned to that incorrect value. Each session comprised 5 blocks of 16 trials. The first block was a practice block and was not recorded and meant to minimize practice effects in the test. Therefore, 4 blocks of 16 measurements were recorded per session for a total of 64 individual measurements.

Results. Results were analyzed by t-test comparing mean response times between Baseline and Treatment sessions. Administration of medium chain triglyceride resulted in significant improvement in the Memory Scanning task ($p<0.0001$) as well as the Mental Rotation task (p 0.0497). No significant change was found in simple reaction time. See Table 1.

TABLE 1

| Test | Baseline Mean (ms) | Test Mean (ms) | P-value |
| --- | --- | --- | --- |
| Reaction Time | 536.332 | 510.730 | 0.1564 |
| Memory Scanning | 841.127 | 743.576 | <0.0001 |
| Mental Rotation | 896.654 | 863.626 | 0.0497 |

For the Memory Scanning task, subjects improved in performance with faster reaction time regardless of the set size to be remembered (see FIG. 1).

FIG. 1 shows that 10 grams of medium chain triglycerides improves performance on a Memory Scanning task. Solid squares and solid line represent Baseline response times. Open circles and dashed lines represent Treatment response times. Error bars represent standard error of the mean. * represent $p<0.05$ for individual set sizes.

At each set size the MCT supplemented drink statistically improved performance (see Table 2) as shown in FIG. 1.

TABLE 2

| Mem Scan Set Size | Baseline Mean | Test Mean | P-value | n |
| --- | --- | --- | --- | --- |
| 1 | 642.938 | 537.938 | <0.0001 | 320 |
| 2 | 758.931 | 676.469 | 0.0004 | 320 |
| 3 | 847.769 | 747.413 | <0.0001 | 320 |
| 4 | 889.638 | 771.612 | <0.0001 | 320 |
| 5 | 938.769 | 829.7 | 0.001 | 320 |
| 6 | 968.950 | 898.325 | 0.0267 | 320 |

Example 4

Improvement in Cognitive Function in an Elderly Population with Medium Chain Triglycerides and L-Carnitine The study recruited three elderly subjects, two males and one female. Average age was 57 years. All subjects were free from any significant medical, neurological, or psychiatric illness. Subjects were taking no central nervous system medications. Subjects were asked to fast overnight for approximately 12 hours on the night prior to the study visit. They arrived in the morning and baseline measurements were taken on three tests: a measure of simple reaction time, a memory scanning paradigm and a mental rotation task. Each test included a set of practice measurements which were not recorded. The practice tests are designed to minimize practice effects of repeated testing. The subjects then consumed the test article, waited 1 hour and then all three tests were repeated. The task was designed to test if mixtures of medium chain triglycerides with L-carnitine could improve cognitive performance in an elderly population.

Test article. The test article comprised 10 grams of a 50% medium chain triglyceride/50% corn starch powder and 250 mg of L-carnitine mixed with Ensure™. The test article delivered a total of 5 grams of medium chain triglycerides with 250 mg of L-carnitine. The subjects were asked to consume the test article in 10 minutes or less.

Reaction time. The reaction time test measured reaction to a stimulus presented on a computer screen. The subject's task was to press the Z key if the stimulus appeared on the left portion of the screen and the/key if the stimulus appeared on the right side of the screen. Reaction time was measured in milliseconds. If the response was incorrect or greater than 1500 milliseconds then the default value of 1500 ms was assigned. Each session comprised 9 blocks of 50 measurements. The first 3 blocks were practice blocks that were not recorded and meant to minimize practice effects in the test. Therefore, 6 blocks of 50 measurements each were recorded per session for a total of 300 individual measurements.

Memory Scanning. The memory scanning task measured the ability of the subject to briefly hold a set of numbers in short term memory. The subject is presented with a set of digits "to be remembered". The number of digits varied between 1 to 6 digits. After a brief delay of 500 ms the subject was then presented with a "probe" digit. The subject's task was to remember if the probe digit was present in the "to be remembered" set of digits. If the probe digit was included in the "to be remembered" set, then subject pressed the/key on the keyboard. If the probe digit was not in the "to be remembered set", the subject pressed the Z key. Both correct answers and the time it takes to respond were recorded. Each session comprised of 6 blocks of 48 trials. The first block was a practice block was not recorded and meant to minimize practice effects in the test. Therefore, 5 blocks of 48 measurements were recorded per session for a total of 240 individual measurements.

Mental Rotation. The mental rotation task measured how quickly the subjects could mentally rotate an object. On each trial, the subject was presented with a symbol resembling an upper-case 'F'. The symbol was presented at one of eight orientations, and was either a letter 'F' or the mirror-image of an 'F'. The subject's task was to determine whether the symbol was a normal or a reversed 'F', and to respond as quickly as possible by pushing the Z key if the symbol was reversed, or the/key if the symbol was not reversed. If the response was incorrect, or if an invalid key was pressed, a brief tone was heard and the maximum time (1500 ms) was assigned to that incorrect value. Each session comprised 5 blocks of 16 trials. The first block was a practice block and was not recorded and meant to minimize practice effects in the test. Therefore, 4 blocks of 16 measurements were recorded per session for a total of 64 individual measurements.

Results. Results were analyzed by t-test comparing mean response times between Baseline and Treatment sessions. Administration of medium chain triglyceride resulted in significant improvement in the Memory Scanning task ($p<0.0001$) as well as the Mental Rotation task ($p<0.0001$). No significant change was found in simple reaction time. See Table 3.

TABLE 3

| Test | Baseline Mean (ms) | Test Mean (ms) | P-value |
| --- | --- | --- | --- |
| Reaction Time | 531.990 | 504.874 | 0.1955 |
| Memory Scanning | 792.529 | 692.958 | <0.0001 |
| Mental Rotation | 873.724 | 796.592 | <0.0001 |

Figure 2:
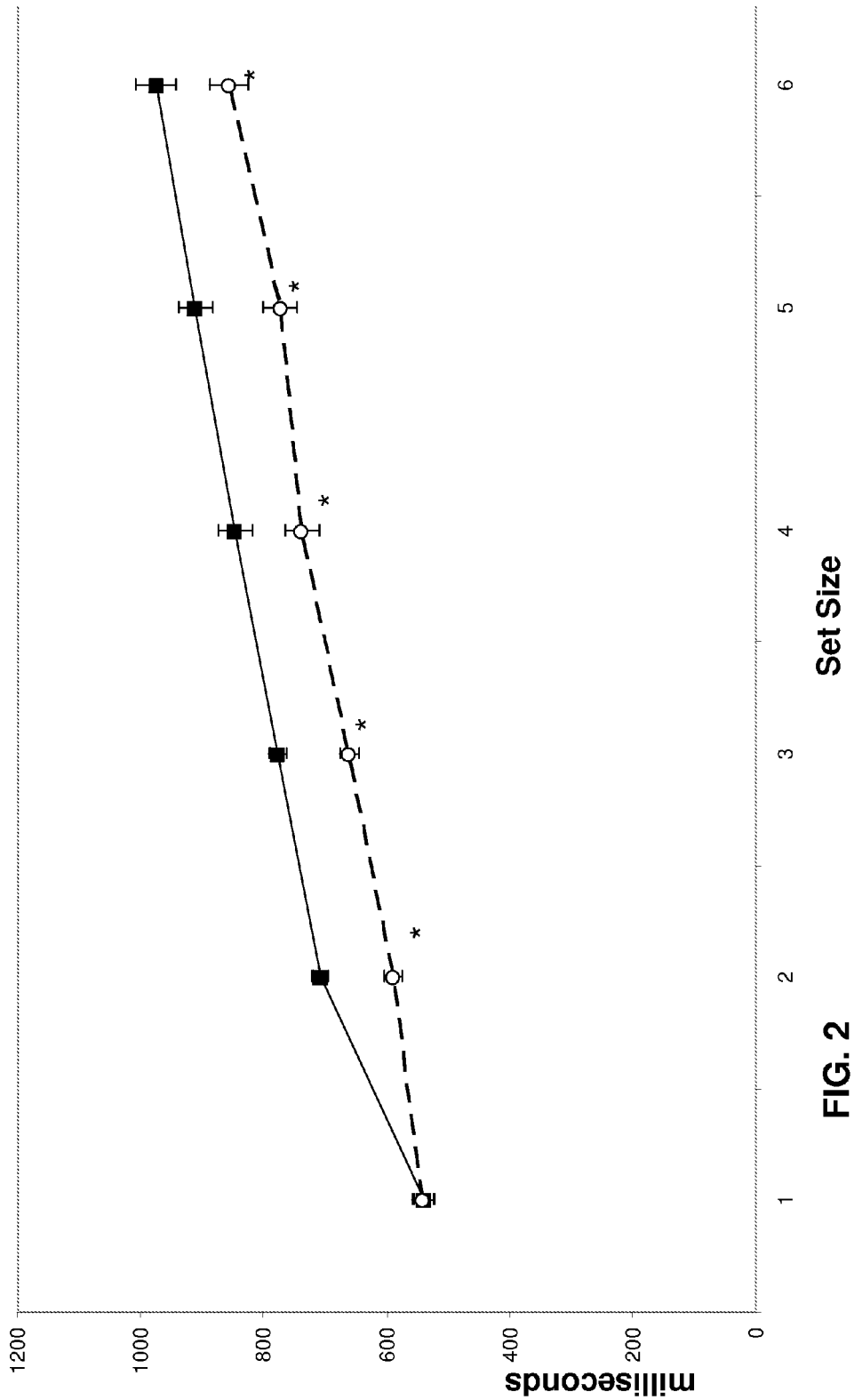
FIG. 2 shows the improvement of mental performance, as measured by the improvements in Memory Scanning Reaction Time for all set sizes for an AAMI cohort.

For the Memory Scanning task, MCT+carnitine improved performance with faster reaction time regardless of the set size to be remembered (see FIG. 2).

FIG. 2 shows that 10 grams of medium chain triglycerides with 250 mg of L-carnitine improves performance on a Memory Scanning task. Solid squares and solid line represent Baseline response times. Open circles and dashed lines represent Treatment response times. Error bars represent standard error of the mean. * represent $p<0.05$ for individual set sizes. At each set size MCT supplemented drink statistically improved performance (see Table 4) as shown in FIG. 2.

TABLE 4

| Mem Scan Set Size | Baseline Mean | Test Mean | P-value | N |
| --- | --- | --- | --- | --- |
| 1 | 539.587 | 541.237 | 0.9453 | 80 |
| 2 | 708.075 | 589.663 | <0.0001 | 80 |
| 3 | 777.125 | 660.55 | <0.0001 | 80 |
| 4 | 845.362 | 737.25 | 0.0055 | 80 |
| 5 | 910.337 | 772.725 | 0.0007 | 80 |
| 6 | 974.688 | 856.325 | 0.0098 | 80 |

Example 5

Improvement in Cognitive Function in Subjects Diagnosed with Age Associated Memory Impairment (AAMI) Treated with Medium Chain Triglycerides A randomized, double-blind, placebo-controlled, parallel group, multi-center design study of a medium chain triglyceride (Ketasyn™) for Age Associated Memory Impairment was conducted.

Study Overview. 159 outpatients diagnosed as having AAMI were enrolled in the study. Sixty-two (62) male and ninety-seven (97) female subjects between ages 50 and 85 were enrolled. Mean age was 65 years of age.

Study Screening Measures. The following tests and rating scales were used as screening measures to select subjects with AAMI and to exclude subjects with dementia or Mild Cognitive Impairment (MCI).

Memory Assessment Clinics Questionnaire (MAC-Q). This is a five item memory questionnaire on which subjects are asked to rate on a five point scale the extent to which they have experienced memory loss since early adulthood when performing important tasks of daily life.

Geriatric Depression Scale (GDS). This scale consists of 30 questions (e.g. Are you basically satisfied with your life?), each of which is checked yes or no by the subject. A score of 11 or higher has been shown indicative of depression.

Mini-Mental State Examination (MMSE). This is probably the most widely used brief instrument for identifying subjects with dementia. The subject is asked to answer questions related to orientation (e.g. Where are you now?) and perform a series of simple cognitive tasks.

Wechsler Memory Scale-Revised (WMS-R)— Logical Memory Subtest I. This is a widely used screening measure in which the subject is asked to recall verbatim a brief story just after hearing it. A score between 19 and 11 (inclusive) qualifies the individual for admission to the study. In that case, or if the individual scores 10 or lower, the two following tests are not administered.

Wechsler Memory Scale-Revised (WMS-R)— Verbal Paired Associates I. In this test, a list of eight words is read to the subject. Some of these words are "easy" to associate with one another (e.g. baby-cries) and others are more abstract (e.g. cabbage-pen) and thus "hard" to associate. After the eight pairs are read, the first word in each pair is read in a different order, and the subject is asked to provide the associated word. This procedure is continued for three trials and the "easy" and "hard" associates are scored separately. A score of 6 or less on the "hard" associates qualifies a potential subject for admission. In that case, the following test is not administered.

Wechsler Memory Scale-Revised (WMS-R)— Visual Paired Associates I. This is the visual analog of the test described above. In this case, subjects are shown six abstract line drawings, each paired with a different color and then asked to indicate the appropriate color associated with each figure. As in the verbal paired associates test, the procedure continues for three trials. A score of 12 or less qualifies the subject for admission in the study.

The study entailed a screening visit to determine if the subject was eligible for the study based on the inclusion/exclusion criteria. If the subject met inclusion criteria and was not excluded based on exclusion criteria, they were seen in the clinic within 21 days of the screening visit for baseline evaluation on all tests that served as outcome measures (Visit 2). Following baseline evaluation, subjects were provided with a 35 day supply of either Ketasyn™ 20 gm daily, or matching placebo and were scheduled for a follow-up visit 30 days (+3) later (Visit 3). On Visit 3, all outcome measures were again administered and any adverse events recorded. Ketasyn™ dosage was increased to 40 gm daily for the remainder of the study. Visits 4 and 5 followed at 30 day (±3) intervals and on each occasion all outcome measures were administered and adverse events recorded. Treatment was terminated at Visit 5. Visit 6 occurred 14 days (±3) days following Visit 5 and all outcome measures were administered.

Evaluations at the study site were scheduled to occur 6 times: at Screen, Baseline, and post-baseline days 30, 60, 90 and 104. Clinic were scheduled in the morning, with the subject receiving their daily dose (Baseline, Days 30, 60 and 90) at the clinic following the pre-dose blood sample.

Dosing overview. During the double-blind period of the protocol, 79 subjects received Ketasyn™, and 75 subjects received placebo. Ketasyn is a free flowing powder consisting of 50% medium chain triglycerides (MCT) and 50% corn starch. The medium chain triglycerides are composed of approximately 50% C8 and 50% C10 carbon chains. Therefore, a 20 gram dose of Ketasyn delivered a 10 gram dose of MCT and a 40 gram dose delivered a 20 gram dose of MCT.

Placebo was an isocaloric mix of Long Chain Triglcyerides (LCT) and protein. The LCT were derived from Centennial IX (Diehl Inc. OH) and is composed of Soybean oil emulsified with mono- and di-glycerides. The protein source is whey protein isolate (Davisco Inc., Eden Paire, Minn.). The nutritional profile of the Placebo is 60% protein, 31% fat, and 9% carbohydrate.

Study compound was 20 gm of Ketasyn™, or matching placebo powder mixed in one (1) glass of a liquid (i.e. preferably Ensure™; approximately 8 oz) QD for the first thirty (30) days of treatment. On Day 31, each subject took 40 gm of Ketasyn™ or placebo QD and continue through Day 90. QD doses were administered in the morning, during breakfast, except on clinic visit days (Baseline, Days 30, 60 and 90) when the subject was asked to undergo an overnight fast prior to the visit, and study doses were administered in the clinic. On clinic day visits, study compound was mixed with low glycemic drink, (i.e. water or preferably Atkins Advantage™ Ready to Drink Shakes).

Genotyping. Subjects in the study were asked to consent to genotyping for allelic variation in the coding regions of the apolipoprotein E gene. Allelic variants in the apolipoprotein E gene are known risk factors for Alzheimer's disease and may influence the efficacy of treatments.

Efficacy measures. Efficacy outcomes included:

First-Last Names Association Test (FLN(Youngjohn, J. R., et al., First-Last Names and the Grocery List Selective Reminding Test: two computerized measures of everyday verbal learning, *Arch Clin Neuropsychol,* 1991, 6:287-300))- Immediate and Delayed Recall. In this test from the Psychologix Battery, subjects are presented with a series of six pairs of first and last names that appear, one at a time on the computer screen. Subjects are asked to read each pair as it appears. After the last pair appears, each last name appears (in a different order) and the subject is asked to provide the corresponding first name. This procedure is repeated for three learning trials, which are followed 30 minutes later by a delayed-recall trial. FLN is administered to the subject at Screening, Baseline (Visit 2), and Treatment Days 30 (Visit 3), 60(Visit 4), 90 (Visit 5) and 104 (Visit 6).

Serum Ketone body levels. Serum Ketone body levels were elevated after treatment with medium chain triglycerides. Ketone body levels were measured enzymatically by determining the level of beta-hydroxybutyrate present in the serum at both pre-dose and 2 hours post dose. See Table 5.

TABLE 5

| Visit | Placebo BHB in mM (SD) | MCT BHB in mM (SD) | Amount of Active* or Placebo |
|---|---|---|---|
| Baseline Predose | 0.1120(0.0752) | 0.1223(0.1064) | |
| Baseline 2 hr Postdose | 0.1113(0.0425) | 0.1885(0.1202) | 20 g |
| Day 30 Predose | 0.0868(0.0362) | 0.0929(0.0593) | |
| Day 30 2 hr Postdose | 0.0994(0.0316) | 0.1737(0.0815) | 20 g |
| Day 60 Predose | 0.0859(0.0447) | 0.0919(0.0526) | |
| Day 60 2 hr Postdose | 0.1037(0.0363) | 0.2465(0.1356) | 40 g |
| Day 90 Predose | 0.0846(0.0556) | 0.0865(0.0593) | |
| Day 90 2 hr Postdose | 0.0968(0.033) | 0.2189(0.1605) | 40 g |
| Day 104 Predose | 0.0758(0.0325) | 0.0861(0.0609) | |

*Active 50% MCT powder.

Outcomes

FLN TC1

On Day 90, ApoE4+ subjects taking medium chain triglycerides (n=17) improved from Baseline in the FLN immediate recall task trial 1 0.89525 points, while those taking Placebo (n=18) had a mean decline of −0.318 (2 way ANOVA using treatment and ApoE4+ status, p-value=0.0012).

On Day 104, ApoE4+subjects taking medium chain triglycerides (n=17) improved from Baseline in the FLN immediate recall task trial 1 0.9412 points, while those taking Placebo (n=18) had a mean decline of 0.0556, (2 way ANOVA using treatment and ApoE4 status, p-value=0.0096).

Across all study visits, there was a significant correlation in ApoE4(−) subjects taking medium chain triglycerides (n=47) between Age and change from Baseline in the FLN immediate recall task trial 1 ($r2$ 0.03473, p-value=0.0093). On the contrary, in the Placebo group there were no significant correlation in ApoE4(−) subjects (n=45) between Age and change from Baseline in the FLN immediate recall task trial 1 ($r2$ 0.009808, p-value=0.1811).

Across all study visits there was a significant difference in subjects who identified their ethnicity as "black". Black subjects taking medium chain triglycerides (n=2) improved an average of 0.75 points in the FLN immediate recall task trial, while those in the Placebo group (n=4) declined an average of −0.25 points (ANOVA using treatment in black ethnicity, p-value=0.0257).

On Day 90, there was a significant difference in subjects who identified their ethnicity as "black". Black subjects taking medium chain triglycerides (n=2) improved an average of 1 point in the FLN immediate recall task trial 1, while those in the Placebo group (n=4) declined an average of −0.5 points (ANOVA using treatment in black ethnicity, p-value=0.0257).

On Day 90, there was a significant difference in subjects who were of the apolipoprotein E genotype 4/3. 4/3 subjects taking medium chain triglycerides (n=13) improved an average of 0.76923 points in the FLN immediate recall task trial 1, while in the Placebo group subjects of the genotype 4/3 (n=16) declined an average of −0.1875 points (ANOVA using treatment in 4/3 genotype, p-value=0.0158).

FLN TC2

Across all study visits, there was a significant correlation in ApoE4(−) subjects taking medium chain triglycerides (n=47) between Age and change from Baseline in the FLN immediate recall task trial 2 ($r2$ 0.024089, p-value 0.0307). On the contrary, in the Placebo group there were no significant correlation in ApoE4(−) subjects (n=45) between Age and change from Baseline in the FLN immediate recall task trial 2 ($r2$ 0.000267, p-value=0.8258).

Across all study visits, there was a significant correlation in ApoE4(+) subjects taking medium chain triglycerides (n=17) between Age and change from Baseline in the FLN immediate recall task trial 2 ($r2$ 0.080484, p-value=0.0173). On the contrary, in the Placebo group there were no significant correlation in ApoE4(+) subjects (n=18) between Age and change from Baseline in the FLN immediate recall task trial 2 ($r2$ 0.012599, p-value=0.3479).

On Day 30, there was a significant correlation in ApoE4(+) subjects taking medium chain triglycerides (n=17) between Age and change from Baseline in the FLN immediate recall task trial 2 ($r2$ 0.336024, p-value=0.0147). On the contrary, in the Placebo group there were no significant correlation in ApoE4(+) subjects (n=18) between Age and change from Baseline in the FLN immediate recall task trial 2 on Day 30 ($r2$ 0.000087, p-value=0.9707).

Across all study visits on which subjects received study medication, there was a significant correlation in ApoE4(+) subjects taking medium chain triglycerides (n=17) between Age and change from Baseline in the FLN immediate recall task trial 2 ($r2$ 0.082066, p-value=0.0415). On the contrary, in the Placebo group there were no significant correlation in ApoE4(+) subjects (n=18) between Age and change from Baseline in the FLN immediate recall task trial 2 ($r2$ 0.010056, p-value=0.4706).

Across all study visits, there was a significant difference in subjects who were of the apolipoprotein e genotype 4/2. 4/2 subjects taking medium chain triglycerides (n=3) improved an average of 0.5 points in the FLN immediate recall task trial 2, while 4/2 subjects in the Placebo group (n=2) declined an average of −2.125 points (ANOVA using treatment in 4/2 subjects, p-value <0.001).

FLN TC3

Across all study visits, there was a significant correlation in ApoE4(+) subjects taking medium chain triglycerides (n=17) between Age and change from Baseline in the FLN immediate recall task trial 3 ($r2$ 0.109441, p-value=0.0052). In the Placebo group there were no significant correlation in ApoE4(+) subjects (n=18) between Age and change from Baseline in the FLN immediate recall task trial 2 ($r2$ 0.012996, p-value=0.3403).

On Day 30, there was a significant correlation in ApoE4(+) subjects taking medium chain triglycerides (n=17) between Age and change from Baseline in the FLN immediate recall task trial 3 ($r2$ 0.242898, p-value=0.0444). On the contrary, in the Placebo group there were no significant correlation in ApoE4(+) subjects (n=18) between Age and change from Baseline in the FLN immediate recall task trial 2 on Day 30 ($r2$ 0.0043652, p-value=0.4054).

Across all visits, there was a significant difference in subjects who were of the apolipoprotein e genotype 4/2. 4/2 subjects taking medium chain triglycerides (n=3) improved an average of 1.5833 points in the FLN immediate recall task trial 3, while 4/2 in the Placebo group (n=2) declined −2.125 points (ANOVA using treatment in 4/2 subjects, p-value <0.0007).

FLN Delayed

On Day 90, subjects taking medium chain triglycerides (n=79) improved an average of 0.5 points in mean change from Baseline on the FLN delayed recall task, while those taking Placebo (n=76) showed no improvement with a mean change from Baseline of 0.0 (ANCOVA comparing means, treatment, age, site, treatment*site interaction and baseline covariate in model, p-value=0.0416).

On Day 90, ApoE4− subjects taking medium chain triglycerides (N=47) improved an average of 0.68574 points in mean change from Baseline in the FLN delayed task, while those taking Placebo (n=45) declined an average of −0.08918 points (2 way ANOVA, treatment and ApoE4 status p-value=0.0124).

On Day 90, ApoE 3/3 subjects taking medium chain triglycerides (n=37) improved an average of 0.8108 points in change from Baseline in the FLN delayed task, while 3/3 subjects on Placebo (n=37) improved only an average of 0.1081 points (ANOVA using treatment in 3/3 subjects, p-value=0.0393).

On Day 90, female subjects taking medium chain triglycerides (n=46) improved an average of 0.667 points from Baseline in the FLN delayed task, while those taking Placebo (n=51) declined an average of −0.184 points from Baseline in the FLN delayed task (ANOVA using treatment in female subjects, p-value=0.0068).

Across all visits, ApoE 4/2 subjects taking medium chain triglycerides (n=3) improved an average of 1.5833 points in change from Baseline in the FLN delayed task, while those 4/2 subjects taking Placebo (n=2) had a mean decline of −2.125 points (ANOVA using treatment in 4/2 subjects, p-value=0.0007).

Name-Face Association Test (NFA)—Immediate and Delayed Recall

In this test, also from the Psychologix Battery, subjects are presented with a live video presentation of individuals introducing themselves by common first names. After a series of introductions, recall is assessed by showing the same individuals in a different order and asking the subject to provide the name of each person. There are two learning trials in which fourteen name-face pairs are presented and recall is assessed. Delayed recall is assessed thirty minutes later. NFA is administered to subjects at Screening, Baseline (Visit 2), and Treatment Days 30 (Visit 3), 60 (Visit 4), 90 (Visit 5) and 104 (Visit 6).

Outcomes

NFA 14A

Across all study visits, there was a significant correlation in subjects taking medium chain triglycerides (n=79) between Age and change from Baseline in the NFA immediate recall task trial A ($r2$ 0.013446. p-value=0.0364). On the contrary, in the Placebo group (n=76) there were no significant correlation in subjects between Age and change from Baseline in the NFA immediate recall task trial A ($r2$ 0.0.000005, p-value=0.9693).

Across all study visits, there was a significant correlation in ApoE4− subjects taking medium chain triglycerides (n=47) between Age and change from Baseline in the NFA immediate recall task trial A ($r2$ 0.033094. p-value=0.0111). On the contrary, in the Placebo group (n=45) there were no significant correlation in subjects between Age and change from Baseline in the NFA immediate recall task trial A ($r2$ 0.005132, p-value=0.3339).

NFA 14B

Across all study visits, ApoE4− subjects taking medium chain triglycerides (n=47) improved an average of 0.639 points on NFA immediate recall task trial B, while those taking Placebo (n=45) declined an average of −0.136 points (ANOVA using treatment in ApoE4− subjects, p=0.0048).

On Day 30, ApoE4− subjects taking medium chain triglycerides (n=47) improved an average of 0.40426 points on NFA immediate recall task trial B, while those taking Placebo (n=45) declined an average of −0.8 points (ANOVA using treatment in ApoE4− subjects, p=0.0225).

On Day 90, there was a significant correlation in subjects taking medium chain triglycerides (n=79) between Age and change from Baseline in the NFA immediate recall task trial B ($r2$ 0.051901, p-value=0.0435). On the contrary, in the Placebo group (n=75) there were no significant correlation in subjects between Age and change from Baseline in the NFA immediate recall task trial B ($r2$ 0.015814, p-value=0.2791).

Across all study visits, there was a significant correlation in subjects taking medium chain triglycerides (n=79) between Age and change from Baseline in the NFA immediate recall task trial B ($r2$ 0.01722. p-value=0.0178). On the contrary, in the Placebo group (n=76) there were no significant correlation in subjects between Age and change from Baseline in the NFA immediate recall task trial B ($r2$ 0.000005, p-value=0.9678).

Across all study visits, there was a significant correlation in ApoE4− subjects taking medium chain triglycerides (n=47) between Age and change from Baseline in the NFA immediate recall task trial B ($r2$ 0.0261. p-value=0.0244). On the contrary, in the ApoE4-Placebo group (n=45) there were no significant correlation in subjects between Age and change from Baseline in the NFA immediate recall task trial B ($r2$ 0.005845, p-value=0.3023).

NFA 14D

Across all study visits, there was a significant correlation in subjects taking medium chain triglycerides (n=79) between Age and change from Baseline in the NFA delayed recall task ($r2$ 0.017714, p-value=0.0162). On the contrary, in the Placebo group (n=76) there were no significant correlation in subjects between Age and change from Baseline in the NFA delayed recall task ($r2$ 0.005497, p-value=0.1922).

Telephone Dialing Test (TDT)

This is a test of "working memory" from the Psychologix Battery, in which the individual must hold information in mind only long enough to perform a task. In this case the task is to dial a seven or ten digit number on a touch screen representation of a telephone after it has appeared on the testing screen. On some trials the individual encounters interference in the form of a "busy signal" and must redial the number from memory. TDT is administered to subjects at Screening, Baseline (Visit 2), and Treatment Days 30 (Visit 3), 60 (Visit 4), 90 (Visit 5) and 104 (Visit 6).

TDT without Interference

Across all visits, there was a significant difference in subjects who were taking medium chain triglycerides and had six years of education. Subjects with 6 years of education taking medium chain triglycerides (n=8) improved an average of 0.37966 points in the TDT without interference trial, while subjects with six years of education taking the Placebo (n=4) declined −0.04197 points (ANOVA using treatment in 4/2 subjects, p-value <0.0314).

TDT Before Interference

Across all visits, there was a significant correlation between age and change from Baseline in the TDT before interference trial in ApoE4+ subjects who were taking medium chain triglycerides. There was a significant correlation in ApoE4+ subjects taking medium chain triglycerides (n=17) between Age and change from Baseline in the TDT before interference trial ($r2$ 0.068747, p-value=0.0283). On the contrary, in the Placebo group (n=18) there were no significant correlation in ApoE4+ subjects between Age and change from Baseline ($r2$ 0.006418, p-value=0.5035).

Across all visits, there was a significant correlation between age and change from Baseline in the TDT before interference trial in subjects who identified themselves as "white" and were taking medium chain triglycerides. There was a significant correlation in white subjects taking medium chain triglycerides (n=72) between Age and change from Baseline in the TDT before interference trial ($r2$ 0.015959, p-value=0.0303). On the contrary, in the Placebo group (n=69) there were no significant correlation in white subjects between Age and change from Baseline ($r2$ 0.000374, p-value=0.7496).

Across all visits, there was a significant correlation between age and change from Baseline in the TDT before interference trial in subjects who were male and identified themselves as "white" and were taking medium chain triglycerides. There was a significant correlation in white male subjects taking medium chain triglycerides (n=35) between Age and change from Baseline in the TDT before interference trial ($r2$ 0.03163, p-value=0.0406). On the contrary, in the Placebo group (n=27) there were no significant correlation in white male subjects between Age and change from Baseline ($r2$ 0.007459, p-value=0.3978).

Across all visits, there was a significant correlation between age and change from Baseline in the TDT before interference trial in subjects who were male, of the apolipoprotein e genotype 3/3, and were taking medium chain triglycerides. There was a significant correlation in 3/3 male subjects taking medium chain triglycerides (n=15) between Age and change from Baseline in the TDT before interference trial (r2 0.03163, p-value=0.0406). On the contrary, in the Placebo group (n=11) there were no significant correlation in white male subjects between Age and change from Baseline (r2 0.007459, p-value=0.3978).

TDT After Interference

Across all visits, there was a significant correlation between age and change from Baseline in the TDT after interference trial in subjects who were male, ApoE4−, and were taking medium chain triglycerides. There was a significant correlation in ApoE4− male subjects taking medium chain triglycerides (n=23) between Age and change from Baseline in the TDT before interference trial (r2 0.076249, p-value=0.0077). On the contrary, in the Placebo group (n=14) there were no significant correlation in male, ApoE4− subjects between Age and change from Baseline (r2 0.000003, p-value=0.9892).

Across all visits, there was a significant correlation between age and change from Baseline in the TDT after interference trial in subjects who were male, ApoE 3/3, and were taking medium chain triglycerides. There was a significant correlation in ApoE 3/3 male subjects taking medium chain triglycerides (n=23) between Age and change from Baseline in the TDT before interference trial (r2 0.13174, p-value=0.0051). On the contrary, in the Placebo group (n=15) there were no significant correlation in male ApoE 3/3 subjects between Age and change from Baseline (r2 0.008633, p-value=0.5486).

Visual Sequence Comparison (VSC; (Kay, G., Cogscreen: Professional Manual, 1995))

VSC simultaneously presents the respondent with two alphanumeric strings, one on the right and the other on the left half of the screen. The respondent selects [SAME] or [DIFFERENT] for each pair, indicating whether the same characters are presented in the same order for both sequences. The strings vary in length from four to eight items. For each pair, the strings may differ by one or two items. Half of the 20 sequence pairs present the same sequence, and half present a different sequence. Performance measures include the speed (VSC Speed; VSCRTC) and accuracy (VSC Accuracy; VSCACC) of responses, and the number of problems correctly completed per minute (VSC Thruput; VSCPUT). Most subjects complete almost all problems, therefore Thruput is considered the best measure of efficacy. Mental functions addressed by this test include visual attention, working memory, verbal-sequential processing, and visual-perceptual speed.

The VSC is administered to subjects at Screening, Baseline (Visit 2), and Treatment Days 30 (Visit 3), 60 (Visit 4), 90 (Visit 5) and 104 (Visit 6).

VSC Thruput

Across all study visits, there was a significant difference in subjects with 2 years of education on VSC thruput task. Subjects with three years of education taking medium chain triglycerides (n=1) improved an average of 3.427 points in the VCS thruput task, while subjects with three years of education in the Placebo group (n=2) declined an average of −0.346 points (ANOVA using treatment in subjects with 3 years of education, p-value=0.0234).

DAT Dual Task (DAT dual)

The second DAT task is the Visual Sequence Comparison task, which is performed simultaneously with the visual monitoring task. Response speed is measured for both the monitoring task (DAT Indicator Dual Speed; DATDRTC) and the visual sequence comparison task (DAT Sequence Comparision Speed; DATSCRTC). Accuracy (DAT Sequence Comparision Accuracy; DATSCACC) and number of items correctly completed per minute (DAT Sequence Comparison Thruput; DATSCPUT) are measured for the sequence comparison task in the dual condition. DAT Indicator Dual Premature Responses (DATDPRE) represents the number of premature centering responses in the simultaneous condition. When the two tasks are presented simultaneously, the test assesses divided attention, working memory, and visual-motor and visual-perceptual speed. Thruput is considered the most accurate measure. The DAT-dual is administered to subjects at Screening, Baseline (Visit 2), and Treatment Days 30 (Visit 3), 60 (Visit 4), 90 (Visit 5) and 104 (Visit 6).

DAT Thruput

Across all visits, there was a significant correlation between age and change from Baseline in the DAT Thruput score in subjects who were taking medium chain triglycerides. There was a significant correlation in subjects taking medium chain triglycerides (n=79) between Age and change from Baseline in the DAT Thruput score (r2 0.025075, p-value=0.0042). On the contrary, in the Placebo group (n=76) there were no significant correlation in subjects between Age and change from Baseline (r2 0.003796, p-value=0.2787).

Across all visits, there was a significant correlation between age and change from Baseline in the DAT Thruput score in male subjects who were taking medium chain triglycerides. There was a significant correlation in male subjects taking medium chain triglycerides (n=35) between Age and change from Baseline in the DAT Thruput score (r2 0.042436, p-value=0.0042). On the contrary, in the Placebo group (n=27) there were no significant correlation in subjects between Age and change from Baseline (r2 0.005274, p-value=0.4509).

Across all visits, there was a significant correlation between age and change from Baseline in the DAT Thruput score in ApoE4− subjects who were taking medium chain triglycerides. There was a significant correlation in ApoE4− subjects taking medium chain triglycerides (n=47) between Age and change from Baseline in the DAT Thruput score (r2 0.049976, p-value=0.0017). On the contrary, in the Placebo group (n=45) there were no significant correlation in subjects between Age and change from Baseline (r2 0.01203, p-value=0.1383).

MTS

Subjects are presented with a checkerboard (4×4) made up of purple and yellow squares. The checkerboard disappears and is replaced by one identical and one similar board. Subjects are asked to identify the identical board. Response speed, accuracy and efficiency are measured. Performance measures include the speed (MTS Speed) and accuracy (MTS Accuracy; MTSACC) of responses, and the number of problems correctly completed per minute (MTS Thruput; MTSPUT). Most subjects complete almost all problems, therefore Thruput is considered the best measure of efficacy. Mental functions addressed by this test include visual attention, working memory, verbal-sequential processing, and visual-perceptual speed. The MTS is administered to subjects at Screening, Baseline (Visit 2), and Treatment Days 30 (Visit 3), 60 (Visit 4), 90 (Visit 5) and 104 (Visit 6).

On Day 90, there was a significant difference in subjects who identified themselves as "black" on MTS thruput task. Black subjects taking medium chain triglycerides (n=2) improved an average of 15.47 points in the MTS thruput task, while black subjects in the Placebo group (n=4) improved only an average of 3.28 points (ANOVA using treatment in black subjects, p-value=0.0125).

Across all study visits, there was a significant difference in subjects with 3 years of education on MTS Thruput task. Subjects with three years of education taking medium chain triglycerides (n=2) improved an average of 12.46 points in the MTS thruput task, while subjects with three years of education in the Placebo group (n=1) improved only an average of 3.9 points (ANOVA using treatment in subjects with 3 years of education, p-value=0.0216).

Across all study visits, there was a significant difference in subjects with 6 years of education on MTS Thruput task. Subjects with six years of education taking medium chain triglycerides (n=22) improved an average of 2.99 points in the MTS thruput task, while subjects with six years of education in the Placebo group (n=16) improved only an average of 0.602 points (ANOVA using treatment in subjects with 6 years of education, p-value=0.0313).

Across all study visits, there was a significant difference in ApoE4− subjects with 7 years of education on MTS Thruput task. ApoE4− subjects with 7 years of education taking medium chain triglycerides (n=5) improved an average of 4.879 points in the MTS Thruput task, while subjects with six years of education in the Placebo group (n=2) declined an average of −6.713 points (ANOVA using treatment in subjects with 6 years of education, p-value <0.001).

Conclusions The present examples 3, 4 and 5 disclose the novel finding that medium chain triglycerides improved measures of memory, attention and reaction time in an elderly population. This population was free of any dementing illnesses and was categorized as having age associated memory impairment (AAMI). AAMI is considered to occur during the natural course of aging. Mean age for the population in this study was 65.0 years of age. Minimum age was 50, maximum age was 83. The present invention discloses the surprising finding that treatment with 10-20 grams of medium chain triglycerides given once a day is sufficient to improve several measures of brain function. Improvement was found in memory tasks, such as the First Last Name (FLN) task and the Name Face Association (NFA) task. Improvement was also found in attention tasks such as the Dual Attention Task (DAT) and measures of visual processing such as the Matching to Sample (MTS) task. Together these results teach that providing additional energy reserves to the elderly brain improves a variety of cognitive activities.

Example 6

Formulations

Boost™ with fiber nutritional beverage (Mead Johnson Nutritionals) and similar products such as Ensure™ have the following general aspects and ingredients. Amounts are per 8 fl. oz. container, which is planned to provide 20-25% of the daily requirements. Tailoring the following formulation for use in subjects with age associated memory impairment would be very beneficial.

Calories, kcal 250
Calories from fat 70
Protein, g 11
Fat, g 8
Saturated fat, g 1.5
Carbohydrate, g 33
Dietary Fiber, g 3
Sugars, g 16
Water, g 200
Vitamin A, IU 830
Vitamin D, IU 100
Vitamin E, IU 5
Vitamin K, .mcg 23
Vitamin C, mg 30
Folic Acid, .mcg 100
Thiamin, mg 0.37
Riboflavin, mg 0.43
Niacin, mg 5
Vitamin B6, mg 0.5
Vitamin B12, .mcg 1.5
Biotin, .mcg 75
Pantothenic Acid, mg 2.5
Calcium, mg 200
Phosphorus, mg 167
Iodine, .mu.g 25
Iron, mg 3
Magnesium, mg 67
Copper, mg 0.33
Zinc, mg 3.3
Manganese, mg 0.42
Chloride, mg 330
Potassium, mg 330
Sodium, mg 170

The present invention describes a novel formulation wherein the above formula is supplemented with about 1 to 80 grams for medium chain triglycerides and about 10 to 2000 mg of L-carnitine or acetyl-L-camitine. Or more preferably, 5 to 50 grams of medium chain triglycerides and about 50 to 1000 mg of L-carnitine or acetyl-L-camitine. Or more preferably, 10 to 30 grams of medium chain triglycerides and about 100 to 500 mg of L-carnitine or acetyl -L-carnitine.

Example 7

Formulations

Boost™. High Protein Powder (Mead Johnson Nutritionals) or similar products are high-protein, low-fat nutritional powders that can be mixed with skim milk or water. About 54 g of the powder is to be mixed with 8 fluid ounces (fl. oz) of water, and is said to provide at least 25% of the US RDA of most essential vitamins and minerals in 200 calories. It has virtually no fat. When mixed with skim milk, the mixture provides about 290 calories and about 33% of the US RDA of most essential vitamins and minerals. Tailoring the following formulation for use in subjects with age associated memory impairment would be very beneficial.

The water mixture provides the following:
Protein, g 13
Carbohydrate, g 36
Sugars, g 35
Water, g 240
Vitamin A, IU 1290
Vitamin D, IU 33
Vitamin E, IU 10
Vitamin C, mg 20
Folic Acid, .mcg 133
Thiamin, mg 0.4
Riboflavin, mg 0.2
Niacin, mg 6.8
Vitamin B6, mg 0.55
Vitamin B12, .mcg 1
Biotin, .mcg 93
Pantothenic Acid, mg 2.7
Calcium, mg 290
Phosphorus, mg 250
Iodine, .mcg 40

Iron, mg 6
Magnesium, mg 105
Copper, mg 0.7
Zinc, mg 4
Manganese, mg 1
Chloride, mg 220
Potassium, mg 560
Sodium, mg 189

The present invention describes a novel formulation wherein the above formula is supplemented with about 1 to 80 grams for medium chain triglycerides and about 10 to 2000 mg of L-carnitine or acetyl-L-carnitine. Or more preferably, 5 to 50 grams of medium chain triglycerides and about 50 to 1000 mg of L-carnitine or acetyl-L-carnitine. Or more preferably, 10 to 30 grams of medium chain triglycerides and about 100 to 500 mg of L-carnitine or acetyl -L-carnitine.

Example 8

Formulations

Boost™ Pudding (Mead Johnson) or similar products are labeled for intended use in geriatric patients, malnourished cancer patients and persons desiring weight control. The current formulation provides 240 calories in 5 ounces, low sodium and cholesterol, and 15-20% of the US RDA requirements for most vitamins and minerals. Tailoring the following formulation for use in subjects with age associated memory impairment would be very beneficial.
Protein, g 7
Fat, g 9
Saturated Fat, g 1.5
Sugars, g 27
Water, g 92
Vitamin A, IU 750
Vitamin D, IU 60
Vitamin E, IU 4.5
Vitamin C, mg 9
Folic Acid, .mcg 60
Thiamin, mg 0.23
Riboflavin, mg 0.26
Niacin, mg 3
Vitamin B6, .mcg 300
Vitamin B12, .mcg 0.9
Biotin, .mcg 45
Pantothenic Acid, mg 1.5
Calcium, mg 220
Phosphorus, mg 220
Iodine, .mcg 23
Iron, mg 2.7
Magnesium, mg 60
Copper, mg 0.3
Zinc, mg 2.3
Chloride, mg 200
Potassium, mg 320
Sodium, mg 120

The present invention describes a novel formulation wherein the above formula is supplemented with about 1 to 80 grams for medium chain triglycerides and about 10 to 2000 mg of L-carnitine or acetyl-L-carnitine. Or more preferably, 5 to 50 grams of medium chain triglycerides and about 50 to 1000 mg of L-carnitine or acetyl-L-carnitine. Or more preferably, 10 to 30 grams of medium chain triglycerides and about 100 to 500 mg of L-carnitine or acetyl -L-carnitine.

Example 9

Formulations

Nutritional bars have been developed for a variety of diets and activity levels (e.g., Luna.™., from Clif Bar, Inc., Berkeley, Calif.) but have no effect on cognitive performance. An example of such a nutritional bar is shown below. Percents are the portion of minimum daily requirements. Tailoring the following formulation for use in subjects with age associated memory impairment would be very beneficial.
Total Fat, g 4
Saturated Fat, g 3
Sodium, mg 50
Potassium, mg 90
Total Carbohydrate, g 26
Dietary Fiber, g 1
Sugars, g 15
Other Carbs, g 10
Protein, g 10
Vitamin A, % 25
Vitamin C, % 100
Calcium, % 35
Iron, % 35
Vitamin K, % 100
Thiamin, % 100
Riboflavin, % 100
Niacin, % 100
Vitamin B6, % 100
Folic Acid, % 100
Vitamin B12, % 100
Biotin, % 100
Pantothenic Acid, % 100
Phosphorus, % 35
Iodine, % 35
Zinc, % 35
Selenium, % 35
Copper, % 35
Manganese, % 35
Chromium, % 35
Molybdenum, % 35

The present invention describes a novel formulation wherein the above formula is supplemented with about 1 to 80 grams for medium chain triglycerides and about 10 to 2000 mg of L-carnitine or acetyl-L-carnitine. Or more preferably, 5 to 50 grams of medium chain triglycerides and about 50 to 1000 mg of L-carnitine or acetyl-L-carnitine. Or more preferably, 10 to 30 grams of medium chain triglycerides and about 100 to 500 mg of L-carnitine or acetyl -L-carnitine.

Example 10

Formulations

A formulation of flavored gelatin (e.g., JELL-O™) provides 130 calories in 227 g. Tailoring the following formulation for use in active elders would be highly beneficial. Percents are the portion of minimum daily requirements.
Protein, g 2
Fat, g 0
Saturated Fat, g 0
Sugars, g 31
Vitamin A, % 6
Vitamin C, % 4
Calcium, % 0
Iron, % 2
Sodium, mg 75

Gelatin flavors can include: apricot, berry blue, black cherry, cherry, cranberry, cranberry raspberry, cranberry strawberry, grape, lemon, lime, mandarin orange, mango, mixed fruit, orange, peach, peach passion fruit, island pineapple, raspberry, strawberry, strawberry banana, strawberry kiwi, watermelon, wild berry, and wild strawberry, among others.

The present invention describes a novel formulation wherein the above formula is supplemented with about 1 to 80 grams for medium chain triglycerides and about 10 to 2000 mg of L-carnitine or acetyl-L-carnitine. Or more preferably, 5 to 50 grams of medium chain triglycerides and about 50 to 1000 mg of L-carnitine or acetyl-L-carnitine. Or more preferably, 10 to 30 grams of medium chain triglycerides and about 100 to 500 mg of L-carnitine or acetyl-L-carnitine.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of treatment for Age-Associated Memory Impairment (AAMI), comprising the steps of:
    identifying a mammal having, or at risk of AAMI; and
    administering to the mammal a composition comprising medium chain triglycerides (MCT) of the formula:

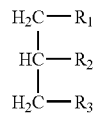

wherein the R1, R2, and R3 esterified to the glycerol backbone are each independently fatty acids having 5-12 carbon chains in an amount effective for the treatment of loss of cognitive function caused by reduced neuronal metabolism in AAMI, and wherein greater than 95% of the R1, R2, and R3 carbon chains are 8 carbons in length, or wherein about 50% of the R1, R2 and R3 carbon chains are 8 carbons in length and about 50% of the R1, R2 and R3 carbon chains are about 10 carbons in length.

2. The method of claim 1 wherein greater than 95% of the R1, R2, and R3 carbon chains are 8 carbons in length.

3. The method of claim 2 wherein the remaining R1, R2, and R3 carbon chains are 6-carbon or 10-carbon chains.

4. The method of claim 1 wherein about 50% of the R1, R2, and R3 carbon chains are 8 carbons in length and about 50% of the R1, R2 and R3 carbon chains are about 10 carbons in length.

5. The method of claim 1, wherein the composition further comprises glucose.

6. The method of claim 1, wherein the medium chain triglyceride is administered in an amount effective to induce hyperketonemia.

7. The method of claim 6, wherein the hyperketonemia results in ketone bodies being utilized for energy in the brain.

8. The method of claim 1 wherein the composition increases the circulating concentration of at least one type of ketone body in the mammal.

9. The method of claim 8, wherein the amount of β-hydroxybutyrate is raised in the blood of the mammal.

10. The method of claim 9, wherein the amount of β-hydroxybutyrate is raised to between about 0.1 millimolar to about 10 millimolar at about two hours post administration.

11. The method of claim 9, wherein the amount of β-hydroxybutyrate is raised to between about 0.15 millimolar to 0.3 millimolar at about two hours post administration.

12. The method of claim 9 wherein urinary excretion level of β-hydroxybutyrate is from about 5 to about 160 mg/dL.

13. The method of claim 1 wherein the composition is administered at a dose of about 0.05 g/kg/day to about 10 g/kg/day.

14. The method of claim 1 wherein the composition is administered at a dose of about 0.1 g/kg/day to about 2 g/kg/day.

15. The method of claim 1, wherein the composition is a ready-to-drink beverage, powdered beverage formulation, nutritional or dietary supplement selected from the group consisting of gelatin capsule or tablet, suspension, parenteral solution, or a food product formulated for human consumption.

16. The method of claim 1, wherein the mammal is a human.

17. The method of claim 1, wherein the administering step is on a regular basis comprising at least once daily.

18. The method of claim 17, wherein the composition is administered as part of a daily treatment regimen for at least about one week.

19. The method of claim 17, wherein the composition is administered as part of a daily treatment regimen for at least about three months.

20. The method of claim 1, comprising the further step of determining the ApoE status of the mammal.

21. The method of claim 20, comprising the further step of selecting a mammal for treatment if the mammal lacks the ApoE4 alleles.

22. The method of claim 1, wherein efficacy for treatment of loss of cognitive function caused by reduced neuronal metabolism in AAMI is determined by results from at least one neuropsychological test.

23. The method of claim 22, wherein the neuropsychological test is selected from the group consisting of Clinical Global Impression of Change (CGIC), Rey Auditory Verbal Learning Test (RAVLT), First-Last Names Association Test (FLN), Telephone Dialing Test (TDT), Memory Assessment Clinics Self-Rating Scale (MAC-S), Symbol Digit Coding (SDC), SDC Delayed Recall Task (DRT), Divided Attention Test (DAT), Visual Sequence Comparison (VSC), DAT Dual Task (DAT Dual), and Geriatric Depression Scale (GDS).

* * * * *